United States Patent
Brauon et al.

(10) Patent No.: US 12,396,718 B2
(45) Date of Patent: Aug. 26, 2025

(54) SELF-STOPPING TISSUE ANCHORS

(71) Applicant: Edwards Lifesciences Innovation (Israel) Ltd., Caesarea (IL)

(72) Inventors: Haim Brauon, Beit Dagan (IL); Yuval Kasher, Kfar Shmuel (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 266 days.

(21) Appl. No.: 18/061,930

(22) Filed: Dec. 5, 2022

(65) Prior Publication Data
US 2023/0101407 A1 Mar. 30, 2023

Related U.S. Application Data

(63) Continuation of application No. PCT/IB2021/053314, filed on Apr. 22, 2021.

(60) Provisional application No. 63/041,423, filed on Jun. 19, 2020.

(51) Int. Cl.
*A61B 17/04* (2006.01)

(52) U.S. Cl.
CPC .. *A61B 17/0401* (2013.01); *A61B 2017/0443* (2013.01); *A61B 2017/0464* (2013.01)

(58) Field of Classification Search
CPC ............... A61B 17/04; A61B 17/0401; A61B 2017/0443; A61B 2017/0464; A61F 2/24
See application file for complete search history.

(56) References Cited

U.S. PATENT DOCUMENTS

| | | | |
|---|---|---|---|
| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |

(Continued)

FOREIGN PATENT DOCUMENTS

| CN | 113331995 A | 9/2021 |
|---|---|---|
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Vi X Nguyen
(74) *Attorney, Agent, or Firm* — Edwards Lifesciences

(57) ABSTRACT

A tissue anchor comprises an anchoring portion, and a crown coupled thereto. The crown includes an anchor head fixedly coupled to the anchoring portion, a driver interface, and a socket. The socket may be fixedly coupled to the driver interface and shaped to receive the anchor head. In a first state the anchor head is seated snugly within the socket, such that torque applied to the driver interface is transferred to the anchoring portion, thereby facilitating screwing of the anchoring portion into the tissue. Screwing of the anchoring portion into the tissue can pull the anchor head distally out of the socket, thereby transitioning the anchor into a second state in which torque applied to the driver interface rotates the socket relative to the anchor head and the anchoring portion. Other embodiments are also described.

15 Claims, 24 Drawing Sheets

(56) References Cited

U.S. PATENT DOCUMENTS

| | | |
|---|---|---|
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |

(56) References Cited

U.S. PATENT DOCUMENTS

| | | |
|---|---|---|
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,604,659 B2 * | 10/2009 | Lee ............... A61B 17/8605 606/319 |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |

(56) References Cited

U.S. PATENT DOCUMENTS

| | | |
|---|---|---|
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |

(56) References Cited

U.S. PATENT DOCUMENTS

| | | |
|---|---|---|
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |

(56) References Cited

U.S. PATENT DOCUMENTS

| | | |
|---|---|---|
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0094355 A1* | 4/2010 | Trenhaile .......... A61B 17/0401 606/232 |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |

(56) References Cited

U.S. PATENT DOCUMENTS

| | | |
|---|---|---|
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2022/0096232 A1 | 3/2022 | Skaro et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new honhydraulic design concept." Urology52.6 (1998): 1151-1154.

(56) References Cited

OTHER PUBLICATIONS

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results 04yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

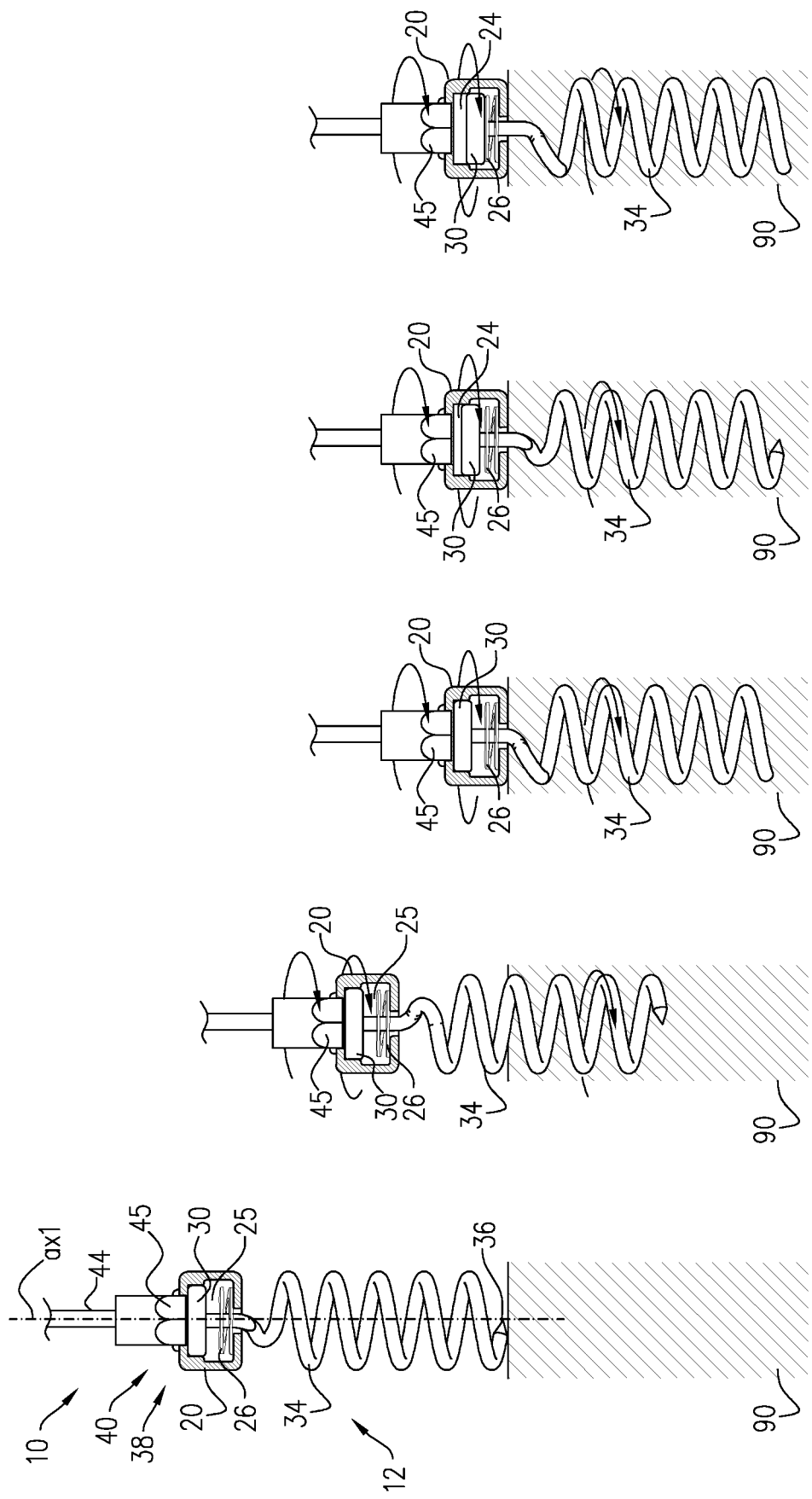

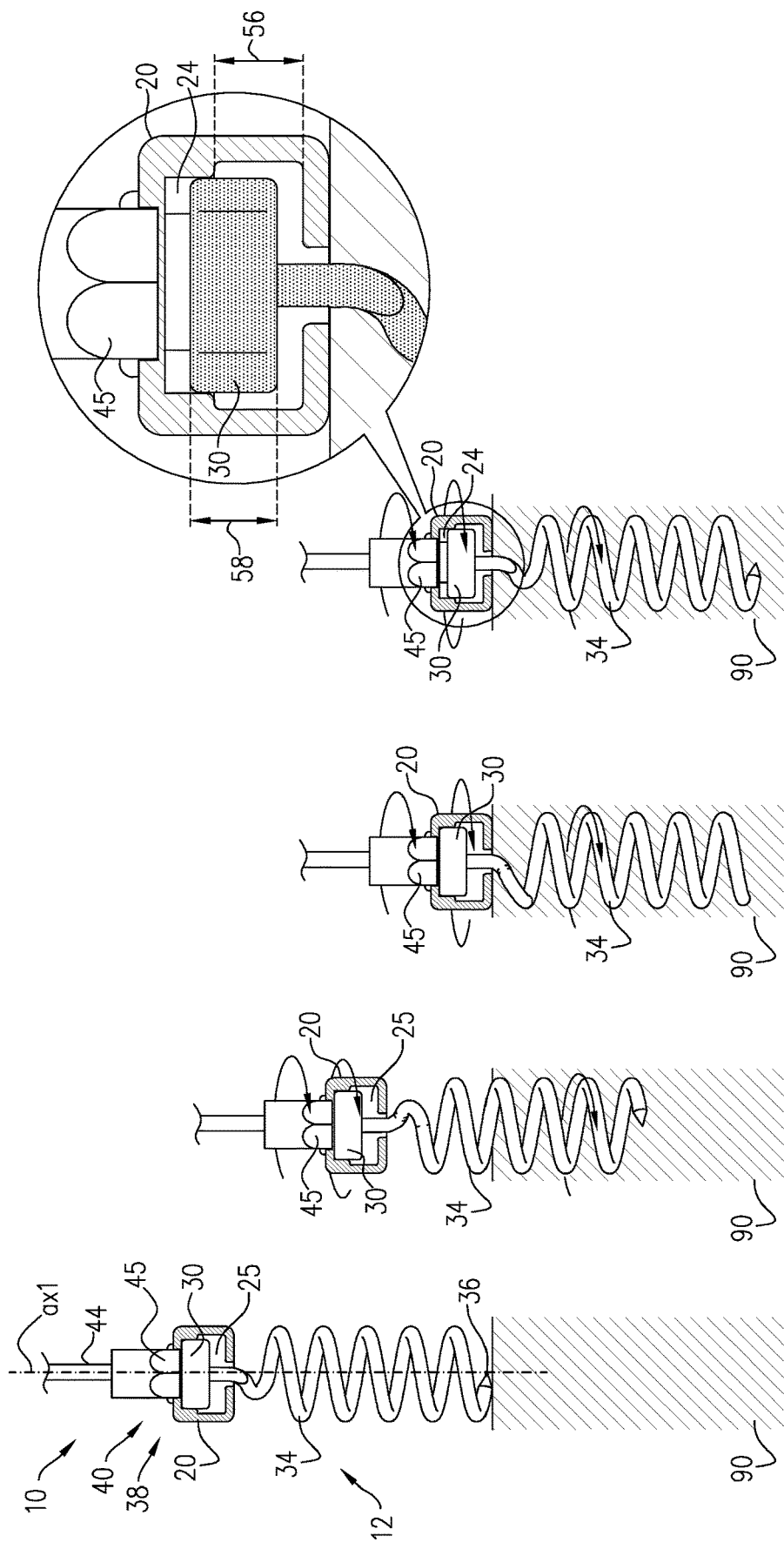

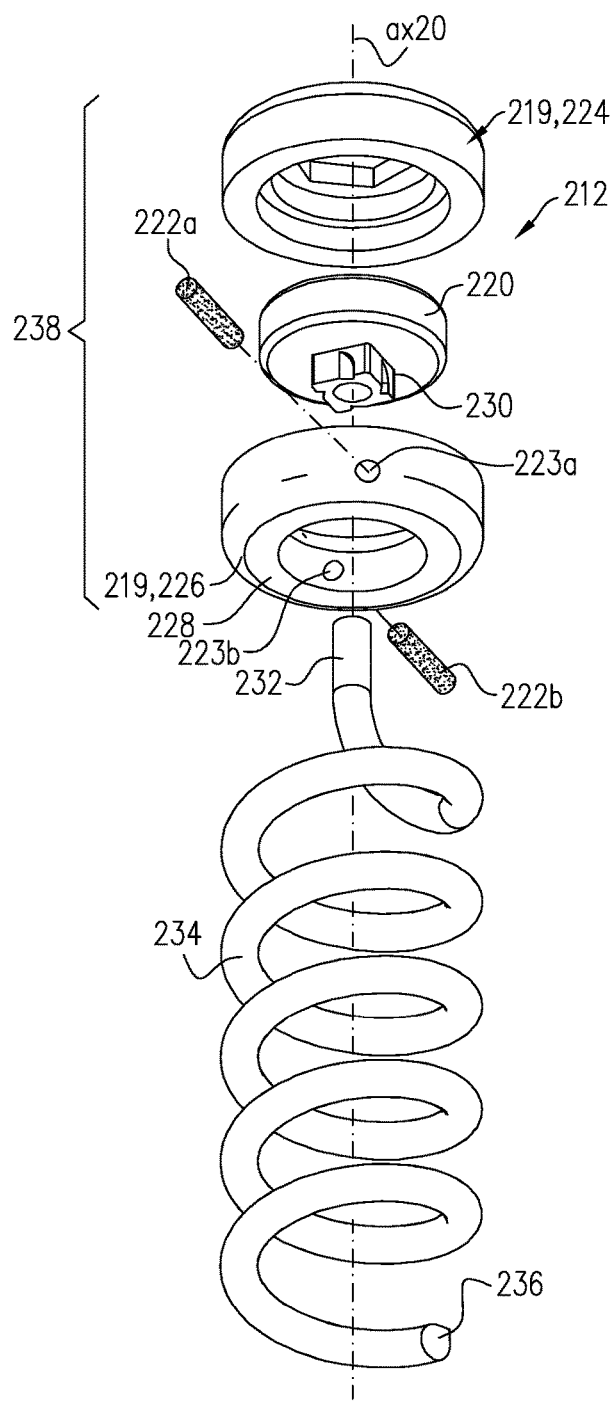
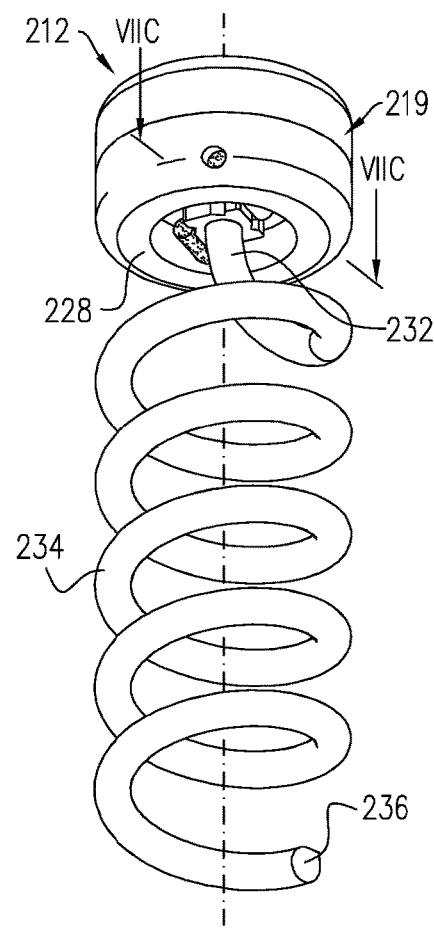
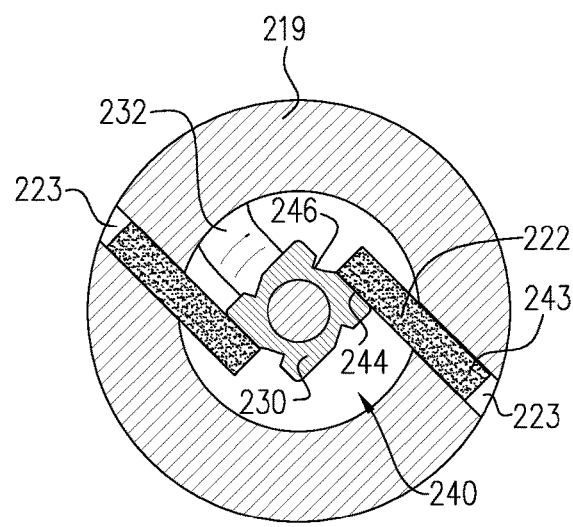
FIG. 7A
FIG. 7B
FIG. 7C

SELF-STOPPING TISSUE ANCHORS

CROSS-REFERENCES TO RELATED APPLICATIONS

The present application is a Continuation of International Patent Application PCT/IB2021/053314 to Brauon et al., filed Apr. 22, 2021, which published as WO 2021/255533, and which claims priority to Provisional U.S. Patent Application 63/041,423 to Brauon et al., filed Jun. 19, 2020, which is incorporated herein by reference.

BACKGROUND

Tissue anchors are useable in a range of medical applications (e.g., for fastening an implant to tissue). Screwable tissue anchors can be configured to translate torque into distal motion, whereby the anchor (e.g., an anchoring portion thereof) is screwed into tissue.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure can be included in the examples summarized here.

Some applications herein are directed to tissue anchors that facilitate controlled anchoring of the tissue anchors into tissue of a subject, such as cardiac tissue. That is, the tissue anchors themselves include features that facilitate such control. For some applications, additional apparatus or system components(s), such as an anchor driver, is provided for screwing an anchoring portion of the tissue anchor into the tissue.

For some applications, a tissue anchor limits a magnitude of torque which can be used to screw the anchor into tissue. For some applications, a tissue anchor limits a depth to which the tissue anchor can be screwed into tissue.

Some tissue anchors described herein can comprise an anchoring portion, and a crown coupled thereto. The crown can include an anchor head, a driver interface, and a socket. The anchor head can be fixedly coupled to the anchoring portion. The socket can be fixedly coupled to the driver interface and can further be shaped to receive the anchor head. In a first state the anchor head is seated snugly within the socket, such that torque applied to the driver interface is transferred to the anchoring portion, thereby facilitating screwing of the anchoring portion into the tissue. Screwing of the anchoring portion into the tissue pulls the anchor head distally out of the socket, thereby transitioning the anchor into a second state in which torque applied to the driver interface rotates the socket relative to the anchor head and the anchoring portion, e.g., such that the torque is no longer transferred to the anchoring portion, e.g., such that further screwing of the anchoring portion into the tissue is not possible.

Some tissue anchors described herein can comprise a crown including an anchor head that is fixedly coupled to the anchoring portion. The crown can define a driver interface configured to be engaged by a driver. The crown can also define a tissue-facing surface, such that screwing the anchoring portion into the tissue moves the tissue-facing surface distally toward the tissue.

For some applications, the crown can comprise a socket that can be fixedly coupled to the driver interface and is shaped to receive the anchor head. For some such applications, the tissue anchor can have (i) a torque-transfer state in which the anchor head is seated within the socket, such that torque applied by the driver to the driver interface rotates the socket, the anchor head, and the anchoring portion, thereby screwing the anchoring portion into the tissue, and (ii) a non-torque-transfer state in which the anchor head is disposed distally from the socket, such that applied torque is not transferred from the interface to the anchor head and the anchoring portion (or is at least significantly reduced).

For such applications, contact between the tissue-facing surface and the tissue can increase resistance against further distal movement of the tissue-facing surface. At this stage, further screwing of the anchor can pull the anchor head distally out of the socket (e.g., towards the tissue-facing surface), such that the tissue anchor transitions from the torque-transfer state to the non-torque-transfer state, thereby limiting the distal force applied by the tissue-facing surface to the tissue.

For some such applications, the tissue anchor can further comprise a spring disposed between the anchor head and the tissue-facing surface. Pulling the anchor head distally out of the socket and towards the tissue-facing surface can compress the spring between the anchor head and the tissue-facing surface, facilitating continued screwing of the anchoring portion into the tissue while the tissue anchor transitions from the torque-transfer state to the non-torque-transfer state.

For some applications, the crown can comprise a slip clutch that transfers torque from the driver interface to the anchor head, while limiting the transferred torque to not exceed a torque threshold.

For some applications in which the crown comprises a slip clutch, the slip clutch can transfer torque from the driver interface to the anchor head via a cantilever pin that revolves, with the anchor head, around the longitudinal axis of the anchor, while a torque-applying portion of the pin remains in contact with a noncircular lateral surface of the anchor head. However, when the applied torque exceeds the torque threshold, the torque-applying portion of the pin deflects away from the anchor head (e.g., due to being pushed laterally outward by the geometry of the anchor head), such that the driver interface and the pin can rotate with respect to the anchor head and the anchoring portion, thereby limiting the transferred torque.

For some such applications, deflection of the torque-applying portion of the pin away from the anchor head is dependent upon whether the applied torque is forward torque or reverse torque. For example, application of forward torque exceeding the torque threshold can cause the pin to deflect. However, application of reverse torque exceeding the torque threshold may not cause the pin to deflect. For example, the pin may revolve in a reverse rotational direction while the pin remains in contact with the anchor head, causing the anchoring portion to unscrew from the tissue. It is hypothesized that, in this way, the anchor can limit torque for screwing of the anchor into the tissue, while reliably allowing sufficient torque for unscrewing of the anchor from the tissue.

For some applications in which the crown comprises a slip clutch, the anchor head comprises a gear shaped to define a lateral surface and a notch. For such applications, the slip clutch transfers torque to the gear via a cantilever pin that revolves, with the anchor head, around the longitudinal axis of the anchor, while a torque-applying portion of the pin remains in contact with the gear. However, when the applied torque exceeds the torque threshold, the torque-applying portion of the pin deflects away from the gear (e.g., due to being pushed laterally outward by the geometry of the anchor head), such that the driver interface and the pin rotate with respect to the gear and the anchoring portion, thereby limiting the transferred torque.

For some such applications, deflection of the torque-applying portion of the pin away from the gear is dependent upon whether the torque is applied to the interface is forward torque or reverse torque. For example, application of forward torque exceeding the torque threshold can cause the pin to deflect away from the gear. However, application of reverse torque exceeding the torque threshold may not cause the pin to deflect. Instead, the pin can revolve in a reverse direction until an end-portion of the pin is latched into the notch defined by the gear. In this way, application of reverse torque causes the gear and the anchoring portion to rotate with the driver interface, causing the anchoring portion to unscrew from the tissue. It is hypothesized that, in this way, the anchor can limit torque for screwing of the anchor into the tissue, while reliably allowing sufficient torque for unscrewing of the anchor from the tissue.

There is therefore provided, in accordance with some applications, a system and/or apparatus for use with tissue of a subject, the system/apparatus including a driver and a tissue anchor, the tissue anchor including an anchoring portion configured to be screwed distally into the tissue by being rotated about a longitudinal axis of the anchor and a crown, coupled to a proximal portion of the anchoring portion, defining a tissue-facing surface.

In some applications, the tissue anchor and/or crown of the tissue anchor includes an anchor head fixedly coupled to the anchoring portion, such that screwing the anchoring portion into the tissue moves the anchor head distally along the longitudinal axis toward the tissue and/or a driver interface, configured to be engaged by the driver.

In some applications, the system/apparatus includes a socket, fixedly coupled to the driver interface, and shaped to receive the anchor head within the socket, the tissue-facing surface facing distally away from the socket.

In some applications, the system/apparatus or tissue anchor thereof has a first state in which the anchor head is seated snugly within the socket, such that torque applied by the driver to the driver interface rotates the socket, the anchor head, and the anchoring portion, thereby facilitating screwing of the anchoring portion into the tissue.

In some applications, the system/apparatus or tissue anchor thereof has a second state in which the anchor head is disposed distally from the socket, such that torque applied by the driver to the driver interface rotates the socket relative to the anchor head and the anchoring portion.

In some applications, the tissue anchor is configured to transition from the first state to the second state, responsively to the anchoring portion having been screwed into the tissue sufficiently deep such that the tissue resists further distal movement of the tissue-facing surface while the screwing of the anchoring portion into the tissue pulls the anchor head distally out of the socket.

In some applications, the driver interface defines a floor that separates the driver from the anchor head while the driver interface is engaged by the driver.

In some applications, the anchor head is shaped such that a transverse cross-section of the anchor head defines a non-circular profile. In some applications, the anchor head is shaped such that the transverse cross-section of the anchor head defines a plurality of lateral surfaces. In some applications, the anchor head is shaped such that the transverse cross-section of the anchor head defines a polygon. In some applications, the anchor head is shaped such that the transverse cross-section of the anchor head defines a square. In some applications, the anchor head is shaped such that the transverse cross-section of the anchor head defines a hexagon.

In some applications, the tissue is tissue of a heart of the subject, and the tissue anchor is transluminally advanceable to the heart.

In some applications, the driver includes a flexible shaft and a driver head at a distal end of the shaft, such that the anchor driver is transluminally advanceable to the heart.

In some applications, the crown includes a casing, the casing dimensioned to define: the driver interface, the socket, the tissue-facing surface, and a free zone disposed between the socket and the tissue-facing surface, and while the anchor is in the second state, the anchor head is disposed within the free zone.

In some applications, the anchor head is configured to rotate with respect to the socket while the anchor head is disposed in the free zone.

In some applications, the driver includes a driver head, the driver head shaped to define a shoulder, the shoulder: positioned on a side of the driver head, and dimensioned such that, while the driver interface is engaged by the driver head, the shoulder contacts a proximal surface of the casing.

In some applications, the system/apparatus includes a spring disposed within the casing, between the anchor head and the tissue-facing surface, and the anchor is configured such that while the anchor transitions from the first state to the second state: screwing the anchoring portion into the tissue pulls the anchor head distally out of the socket, compressing the spring.

In some applications, the anchor is configured such that while the anchor transitions from the first state to the second state, screwing the anchoring portion into the tissue pulls the anchor head distally out of the socket, compressing the spring and pressing the tissue-facing surface against the tissue.

In some applications, the anchor is configured such that while the anchor transitions from the first state to the second state, screwing the anchoring portion into the tissue pulls the anchor head distally out of the socket, compressing the spring while the anchor head is: partially disposed within the socket, and partially disposed within the free zone.

The system and/or apparatus can further comprise an implant, and the tissue anchor can be configured to secure the implant to the tissue. In some applications, the implant comprises a tether or contraction member. In some applications, the tissue anchor is configured to secure the tether or contraction member to the tissue. In some applications, the tissue anchor is configured to secure the tether or contraction member to the tissue such that applying tension to the tether or contraction member changes a shape and/or size of the tissue.

There is further provided, in accordance with some applications, a system and/or apparatus including: a driver, including a shaft and a driver head at a distal end of the shaft; and a tissue anchor. The tissue anchor includes an anchoring portion configured to be screwed distally into the tissue by being rotated about a longitudinal axis of the anchor.

In some applications, the tissue anchor includes a crown, coupled to a proximal portion of the anchoring portion.

In some applications, the tissue anchor and/or crown includes an anchor head fixedly coupled to the anchoring portion, such that rotation of the anchor head rotates the anchoring portion about the longitudinal axis.

In some applications, the tissue anchor, crown, and/or anchor head includes a driver interface, configured to be engaged by the driver head and rotated by the driver.

In some applications, the tissue anchor, crown, and/or anchor head includes a slip clutch. In some implementations, the slip clutch is coupled to the driver interface and/or to the anchor head. In some implementations, the slip clutch is configured to (i) transfer, to the anchor head, torque applied to the driver interface, up to a torque threshold, and to (ii) slip in response to torque greater than the torque threshold applied to the driver interface, thereby limiting torque transferred to the anchor head to not exceed the torque threshold.

In some applications, the anchor head is shaped to define a non-circular lateral surface, the slip clutch includes a cantilever pin, a portion of the cantilever pin fixedly coupled to the driver interface. In some implementations, the slip clutch is configured: (i) to transfer torque from the driver interface to the anchor head by revolving about the longitudinal axis in response to the driver interface rotating while a torque-applying portion of the pin is in contact with the non-circular lateral surface of the anchor head, and (ii) to slip by the pin being deflected away from the longitudinal axis by the anchor head.

In some applications, the slip clutch includes a cantilever pin, a portion of the cantilever pin fixedly coupled to the driver interface, and the slip clutch is configured to slip in response to torque greater than the torque threshold being applied to the driver interface, by the pin being deflected away from the longitudinal axis by the anchor head.

In some applications, the tissue is tissue of a heart of a subject, and the tissue anchor is transluminally advanceable to the heart.

In some applications, the driver includes a flexible shaft and a driver head at a distal end of the shaft, such that the anchor driver is transluminally advanceable to the heart.

In some applications, the slip clutch is configured to selectively rotationally couple the driver interface to the anchor head, such that: (i) in response to application, to the driver interface, of torque in a first rotational direction and at a first magnitude that does not exceed the torque threshold, the anchor head and the anchoring portion rotate with the driver interface in the first rotational direction; in response to application, to the driver interface, of torque in the first rotational direction and at a second magnitude that exceeds the torque threshold, the slip clutch slips such that the driver interface rotates with respect to the anchor head and the anchoring portion; and in response to application, to the driver interface, of torque in a second rotational direction and at the second magnitude, the anchor head and the anchoring portion rotate with the driver interface in the second rotational direction, the second rotational direction being opposite to the first rotational direction.

In some applications, the torque threshold is a first torque threshold, and the tissue anchor is configured such that application, to the driver interface, of torque in the second rotational direction and at a third magnitude exceeding a second torque threshold that is greater than the first torque threshold causes the slip clutch to slip such that the driver interface rotates with respect to the anchor head and the anchoring portion.

In some applications, the anchoring portion is oriented with respect to the slip clutch such that: rotation of the anchor head and the anchoring portion in the first rotational direction facilitates screwing of the tissue anchor into the tissue, and rotation of the anchor head and the anchoring portion in the second rotational direction facilitates unscrewing of the tissue anchor from the tissue.

In some applications, the anchor head is shaped to define a non-circular lateral surface, the slip clutch includes a cantilever pin, a fixed portion of the cantilever pin fixedly coupled to the driver interface. In some implementations, the slip clutch is configured: to transfer torque from the driver interface to the anchor head by revolving about the longitudinal axis in response to the driver interface rotating while a torque-applying portion of the pin is in contact with the non-circular lateral surface of the anchor head, and to slip by the pin being deflected away from the longitudinal axis by the anchor head.

In some applications, the slip clutch is configured such that application of torque to the driver interface, in the first rotational direction and at the first magnitude, causes the anchor head and the anchoring portion to rotate with the driver interface, by the cantilever pin revolving about the longitudinal axis in the first rotational direction with the torque-applying portion ahead of the fixed portion.

In some applications, the slip clutch is configured such that application of torque to the driver interface, in the first rotational direction and at the first magnitude, causes the anchor head and the anchoring portion to rotate with the driver interface, by the cantilever pin revolving about the longitudinal axis in the first rotational direction with the torque-applying portion trailing the fixed portion.

In some applications, the slip clutch is configured such that: the torque-applying portion is a first torque-applying portion, and application of torque to the driver interface, in the first rotational direction and at the first magnitude, causes the anchor head and the anchoring portion to rotate with the driver interface, by the cantilever pin revolving about the longitudinal axis in the first rotational direction while the first torque-applying portion is in contact with the non-circular lateral surface of the anchor head. In some implementations, application of torque, to the driver interface, in the first rotational direction and at the second magnitude, causes the driver interface and the pin to rotate in the first rotational direction, with respect to the anchor head and the anchoring portion, by the pin being deflected away from the longitudinal axis by the anchor head. In some implementations, application of torque, to the driver interface, in the second rotational direction and at the second magnitude, causes the anchor head and the anchoring portion to rotate with the driver interface in the second rotational direction, by the cantilever pin revolving about the longitudinal axis in the second rotational direction while a second torque-applying portion of the pin is in contact with the anchor head.

In some applications, the slip clutch is configured such that: while torque is applied to the driver interface in the first rotational direction and at the first magnitude, the pin has a forward cantilever span between (i) the fixed portion of the pin, and (ii) the first torque-applying portion, and while torque is applied to the driver interface in the second rotational direction, the pin has a reverse cantilever span between (i) the fixed portion of the pin, and (ii) the second torque-applying portion, the forward cantilever span being longer than the reverse cantilever span.

In some applications, the first torque-applying portion is further than the second torque-applying portion from the fixed portion. In some applications, the second torque-applying portion is further than the first torque-applying portion from the fixed portion.

In some applications: the anchor head is shaped to define a notch, the pin defines a pawl, which serves as the second torque-applying portion, and the slip clutch is configured such that application of torque to the driver interface in the second rotational direction and at the second magnitude, causes the anchor head and the anchoring portion to rotate with the driver interface in the second rotational direction, by the cantilever pin revolving about the longitudinal axis in the second rotational direction while the pawl is latched into the notch defined by the anchor head.

In some applications, the slip clutch is configured such that application of torque to the driver interface in the second rotational direction and at the second magnitude, causes the driver interface and the pin to rotate in the second rotational direction, with respect to the anchor head and the anchoring portion, for not more than a quarter turn, before the pawl becomes latched into the notch defined by the anchor head.

The system and/or apparatus can further comprise an implant, and the tissue anchor can be configured to secure the implant to the tissue. In some applications, the implant comprises a tether or contraction member. In some applications, the tissue anchor is configured to secure the tether or contraction member to the tissue. In some applications, the tissue anchor is configured to secure the tether or contraction member to the tissue such that applying tension to the tether or contraction member changes a shape and/or size of the tissue.

There is further provided, in accordance with some applications, a method for use with a tissue of a subject includes advancing a tissue anchor to the tissue, the tissue anchor including an anchoring portion, anchor head, and a driver interface, and screwing the anchoring portion distally into the tissue by applying torque to the driver interface, such that the driver interface and the anchoring portion rotate together about a longitudinal axis of the anchor, continuing to screw the anchoring portion distally into the tissue, at least until the driver interface becomes rotatable relative to the anchor head.

In some applications, the tissue anchor includes a crown coupled to a proximal portion of the anchoring portion, and the crown can include the anchor head, which can be fixedly coupled to the anchoring portion. The driver interface can also be part of the crown in some implementations.

The method can further include engaging a driver (e.g., an anchor driver, etc.) with the driver interface. The method can further include using the driver to screw the anchoring portion distally into the tissue by applying torque to the driver interface, such that the driver interface, the anchor head, and the anchoring portion rotate together about a longitudinal axis of the anchor.

The method can further include, subsequently to screwing the anchor, disengaging the driver from the driver interface and removing the driver from the subject, while leaving the tissue anchor anchored to the tissue.

In some applications, the driver includes a driver head, the driver head shaped to define a shoulder, and screwing the anchoring portion distally into the tissue by applying torque to the driver interface includes screwing the anchoring portion distally into the tissue by applying torque to the driver interface while: the driver head is engaged with the driver interface, and the shoulder is in contact with a proximal surface of the crown.

In some applications, the driver interface defines a floor, and screwing the anchoring portion distally into the tissue by applying torque to the driver interface includes, using the driver head, contacting the floor.

In some applications, the tissue is tissue of a heart of the subject and advancing the tissue anchor to the tissue includes transluminally advancing the tissue anchor to the heart. In some implementations, the tissue is tissue of a mitral valve or a tricuspid valve of a heart.

In some applications, the driver includes a flexible shaft and a driver head at a distal end of the shaft, and the method includes, subsequently to advancing the tissue anchor to the tissue, using the flexible shaft, transluminally advancing the driver head to the driver interface.

In some applications, the crown is shaped to define: a socket fixedly coupled to the driver interface, and a tissue-facing surface facing distally away from the socket; and screwing the anchoring portion distally into the tissue includes screwing the anchoring portion distally into the tissue by applying torque to the driver interface while the anchor head is seated snugly within the socket, such that the driver interface, the socket, the anchor head, and the anchoring portion rotate about the longitudinal axis; and continuing to screw the anchoring portion distally into the tissue includes continuing to screw the anchoring portion distally into the tissue at least until: the tissue resists further distal movement of the tissue-facing surface, and the anchor head becomes pulled distally out of the socket, such that the socket becomes rotatable relative to the anchor head.

In some applications, the crown and/or anchor head is shaped to define a free zone between the socket and the tissue-facing surface, and continuing to screw the anchoring portion distally into the tissue includes continuing to screw the anchoring portion distally into the tissue at least until the anchor head becomes pulled distally into the free zone.

In some applications, continuing to screw the anchoring portion distally into the tissue includes continuing to screw the anchoring portion distally into the tissue at least until the anchor head becomes pulled entirely into the free zone.

In some applications, the tissue anchor includes a spring, the spring disposed between the anchor head and the tissue-facing surface, and continuing to screw the anchoring portion distally into the tissue includes continuing to screw the anchoring portion distally into the tissue at least until the anchor head compresses the spring.

In some applications, continuing to screw the anchoring portion distally into the tissue includes continuing to screw the anchoring portion distally into the tissue at least until the spring presses the tissue-facing surface against the tissue.

In some applications, the crown includes a slip clutch, the slip clutch being coupled to the driver interface and to the anchor head, screwing the anchoring portion distally into the tissue includes screwing the anchoring portion distally into the tissue by applying torque to the driver interface, such that torque is transferred from the driver interface, via the slip clutch, to the anchor head, and continuing to screw the anchoring portion distally into the tissue includes continuing to screw the anchoring portion distally into the tissue at least until, at a torque threshold, the slip clutch slips, such that the driver interface rotates with respect to the anchor head and the anchoring portion.

In some applications, the anchor head is shaped to define a non-circular lateral surface, the slip clutch includes a cantilever pin, a fixed portion of the cantilever pin being fixedly coupled to the driver interface, screwing the anchoring portion distally into the tissue includes screwing the anchoring portion distally into the tissue by applying torque to the driver interface, such that the driver interface and the pin rotate about the longitudinal axis in a first rotational direction, together with the anchor head and the anchoring portion, while a torque-applying portion of the pin presses against the lateral surface of the anchor head. In some implementations, continuing to screw the anchoring portion distally into the tissue includes continuing to screw the anchoring portion distally into the tissue at least until, at the torque threshold, the slip clutch slips by the anchor head deflecting the pin away from the longitudinal axis, such that the driver interface rotates with respect to the anchor head and the anchoring portion.

In some applications, the torque-applying portion of the pin is a first torque-applying portion of the pin, screwing the anchoring portion distally into the tissue includes screwing the anchoring portion distally into the tissue by applying torque to the driver interface, such that the driver interface and the pin rotate about the longitudinal axis in the first rotational direction, together with the anchor head and the anchoring portion, while the first torque-applying portion of the pin presses against the lateral surface of the anchor head. In some implementations, continuing to screw the anchoring portion distally into the tissue includes continuing to screw the anchoring portion distally into the tissue at least until, at the torque threshold, the slip clutch slips by the anchor head pushing against the first torque-applying portion and thereby deflecting the pin away from the longitudinal axis, such that the driver interface rotates with respect to the anchor head and the anchoring portion.

In some applications, the method includes unscrewing the anchoring portion proximally from the tissue, by applying torque in a second rotational direction to the driver interface, such that the anchor head and the anchoring portion rotate with the driver interface, in the second rotational direction while a second torque-applying portion of the pin presses against the anchor head.

In some applications, the anchor head is shaped to define a notch, the pin defines a pawl that serves as the second torque-applying portion, and unscrewing the anchoring portion proximally from the tissue includes unscrewing the anchoring portion proximally from the tissue, by applying torque, in the second rotational direction, to the driver interface, such that the anchor head and the anchoring portion rotate with the driver interface, in the second rotational direction while the pawl is latched into the notch.

In some applications, the methods herein further comprise anchoring an implant, tether and/or contraction member to the tissue. The tissue anchor can be configured to anchor or secure the implant, tether, and/or contraction member to the tissue. In some applications, the tissue anchor is used to anchor or secure the implant, tether, and/or contraction member to the tissue.

Anchoring or securing the implant, tether, and/or contraction member to the tissue can comprise screwing the anchoring portion distally into the tissue by applying torque to the driver interface, such that the driver interface and the anchoring portion rotate together about a longitudinal axis of the anchor, and continuing to screw the anchoring portion distally into the tissue, at least until the driver interface becomes rotatable relative to the anchor head.

In some applications, after anchoring or securing the implant, tether, and/or contraction member to the tissue, the method further comprises applying tension to the tether or contraction member to change a shape and/or size of the tissue (e.g., to change a shape and/or size of an annulus of a heart valve, etc.)

The above method(s) can be performed on a living animal or on a simulation, such as on a cadaver, cadaver heart, simulator (e.g., with the body parts, heart, tissue, etc. being simulated), etc.

The present invention will be more fully understood from the following detailed description of applications thereof, taken together with the drawings, in which:

BRIEF DESCRIPTION OF THE DRAWINGS

FIGS. 1A-E, 2A-H, and 3A-H are schematic illustrations showing example tissue anchor systems and their use, in accordance with some applications;

FIGS. 7A-C, 8A-E and 9A-C are schematic illustrations showing an example tissue anchor system, in accordance with some applications.

DETAILED DESCRIPTION

Figure 1A:
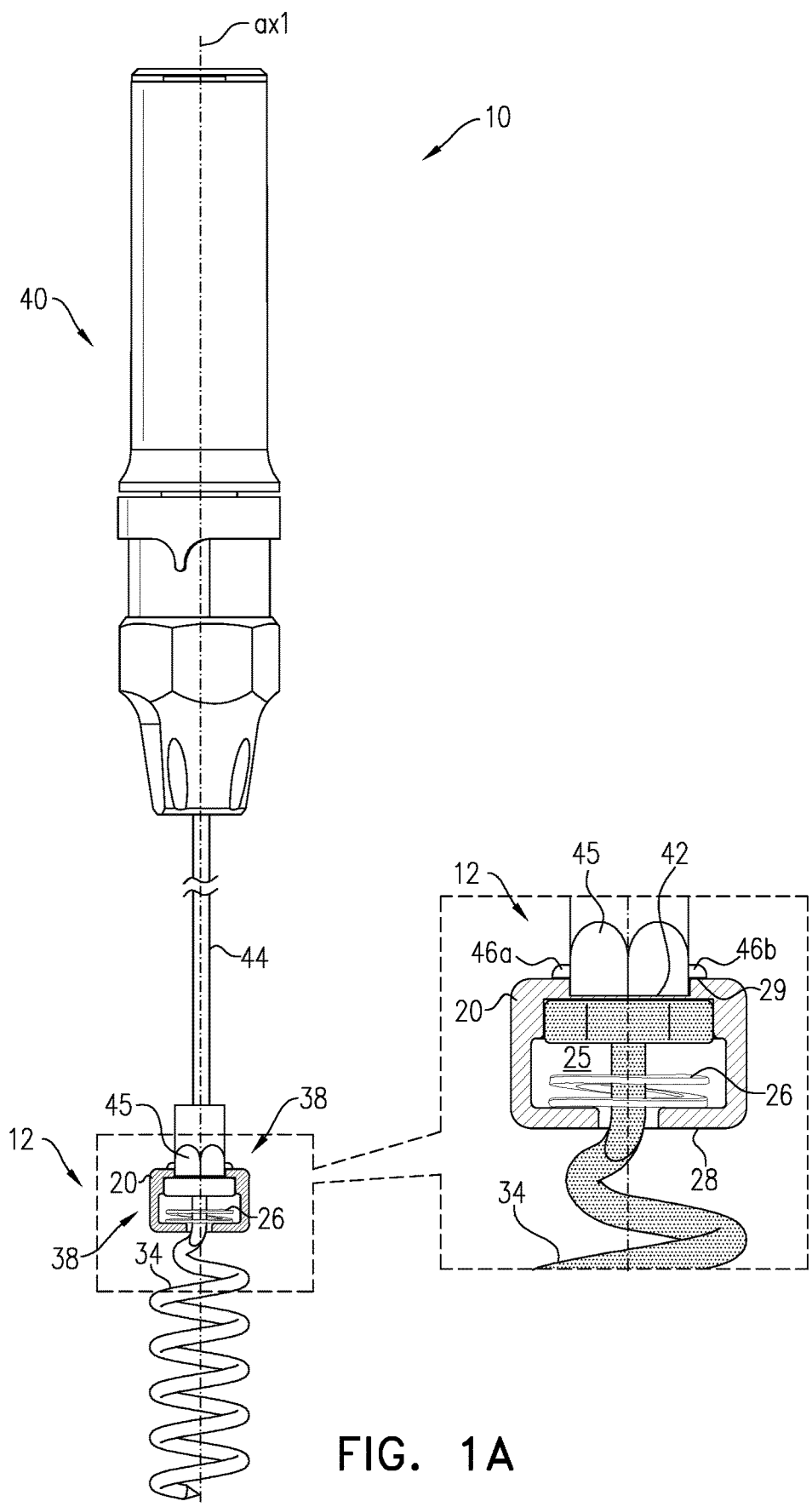

Reference is made to FIGS. 1A-E, 2A-H, and 3A-H, which are schematic illustrations showing use of an example tissue anchor system 10, in accordance with some applications.

System 10 comprises a tissue anchor 12, and an anchor driver 40. As shown, anchor 12 comprises an anchoring portion (i.e., a tissue-engaging element) 34 shaped to facilitate screwing of the anchoring portion into tissue 90 by being rotated about a longitudinal axis ax1 of anchor 12. For example, and as shown, anchoring portion 34 is shaped as a corkscrew having a distal tissue-piercing point 36. This is not meant to exclude other shapes which facilitate anchoring portion 34 being screwed into tissue 90. For example, anchoring portion can be shaped to define a threaded shank.

Figure 1B:
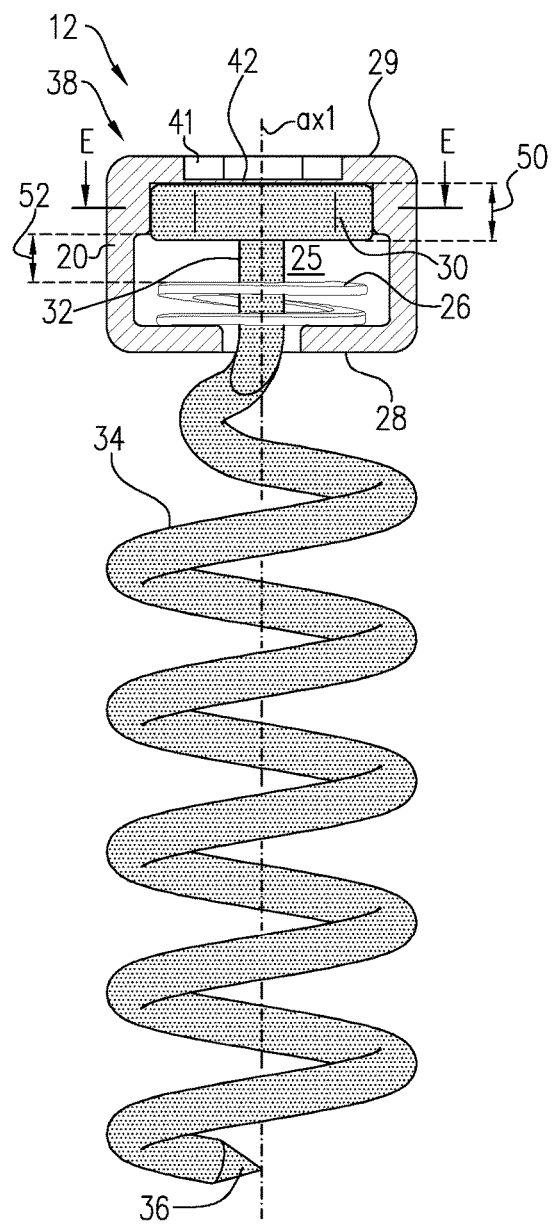
Figure 1C:
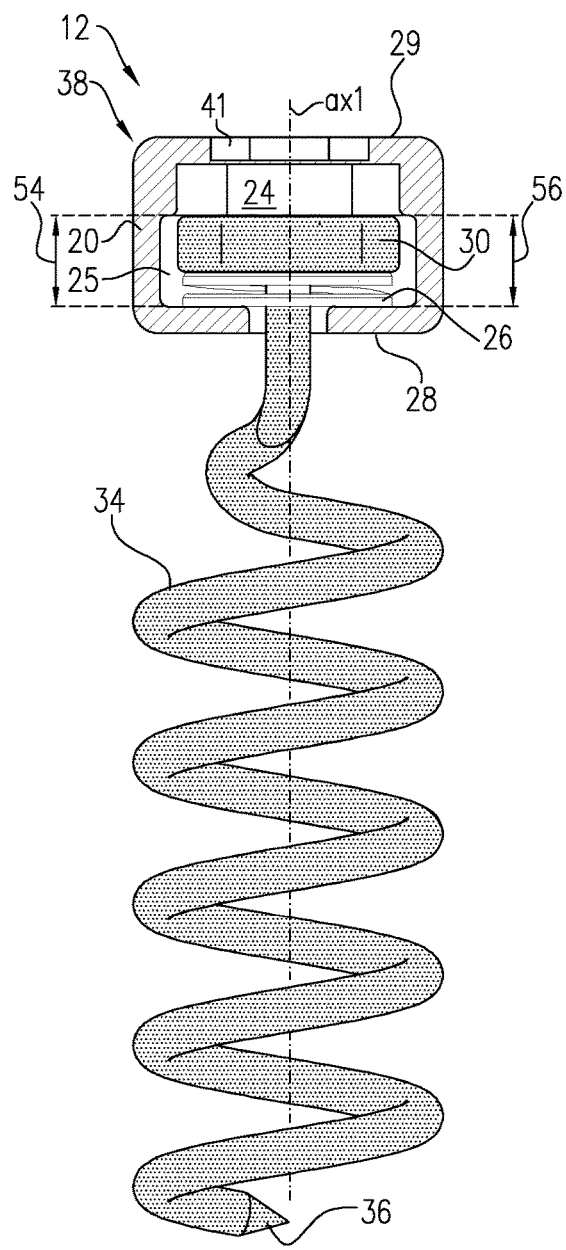
Figure 1D:
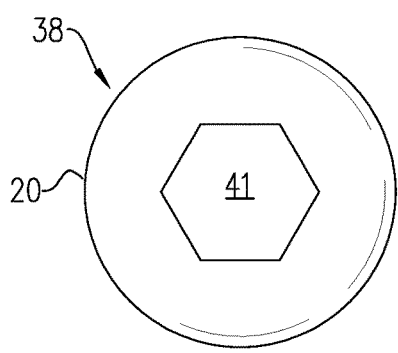
Figure 1E:
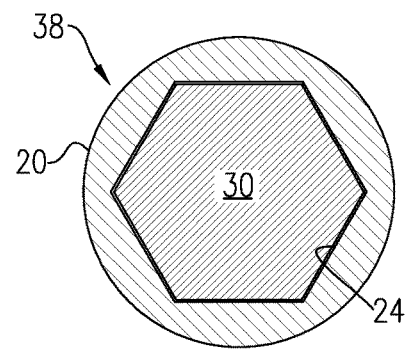

In some applications, and as shown, anchoring portion 34 is coupled, at a proximal portion of the anchoring portion, to a crown 38 that defines a tissue-facing surface 28. FIGS. 1A-C are side-views that show crown 38 in longitudinal cross-section (but anchoring portion 34 is shown whole). FIG. 1D is a top-view of anchor 12, i.e., looking down at crown 38. FIG. 1E is a transverse cross-section through crown 38, at the level indicated in FIG. 1B. As shown, crown 38 comprises an anchor head 30 and a socket 24 shaped to receive the anchor head, e.g., by the anchor head being reversibly seated within the socket. FIG. 1B shows anchor head 30 seated within socket 24, and FIG. 1C shows the anchor head having exited the socket. For some such applications, and as shown in cross-section in FIG. 1E, socket 24 and anchor head 30 are shaped complementarily to each other, such that the socket snugly receives the anchor head.

In some applications, and as shown, crown 38 comprises a driver interface 41 coupled to socket 24 such that the interface and the socket are rotationally fixed. Driver 40 is configured to engage the driver interface 41. For some applications, driver 40 is transluminally advanced to tissue 90 of a subject (e.g., tissue of a heart of the subject), e.g., while coupled to anchor 12. For some such applications, driver 40 having a shaft 44 (e.g., a flexible shaft) facilitates transluminal advancement of the driver to tissue 90.

In system 10, torque is transferred indirectly from driver 40 to anchor head 30, e.g., via driver interface 41 and socket 24. For example, driver 40 can comprise a driver head 45 at a distal end of shaft 44, that is reversibly seatable within driver interface 41 (FIG. 1A). For some applications, and as shown, driver 40 (e.g., driver head 45) does not contact anchor head 30 while driver head 45 is seated within driver interface 41. For example, anchor head 30 can be inaccessible to driver head 45 due to the anchor head being enclosed in a casing 20, e.g., as described hereinbelow.

In some applications, tissue-facing surface 28 faces distally away from socket 24. In some applications, tissue-facing surface 28 is axially fixed in relation to driver interface 41, such that screwing tissue anchor 12 into tissue 90 typically brings surface 28 closer to the tissue (e.g., brings the tissue-facing surface into contact with the tissue). For some applications, tissue-facing surface 28 is also rotationally fixed with respect to driver interface 41 (e.g., tissue-facing surface is fixedly attached to driver interface 41).

For some applications, and as shown, anchor 12 (e.g., crown 38 thereof) comprises casing 20 that comprises socket 24, interface 41 and surface 28. Casing 20 can be a unitary structure that is shaped to define socket 24, interface 41 and surface 28. Casing 20 can house anchor head 30, such that crown 38 comprises both the anchor head and the casing that houses the anchor head. Often for such applications, casing 20 is dimensioned to define a free zone 25 within which anchor head 30 is disposed while the anchor head is not seated in socket 24 (FIG. 1C). Free zone 25 can be disposed distally from socket 24 (i.e., closer than socket 24 to anchoring portion 34). Although socket 24 is configured to transfer torque from interface 41 to anchor head 30 while the anchor head is disposed in the socket (e.g., due to the snug fit therebetween), free zone 25 is configured to allow the socket to rotate with respect to the anchor head while the anchor head is disposed in the free zone and not in the socket (e.g., such that torque is not transferred from the socket to the anchor head).

For some applications, socket 24, interface 41, and surface 28 of casing 20 are rotationally fixed in relation to each other, such that rotation of one part of the casing rotates the entire casing. This is not meant to exclude applications in which tissue-facing surface 28, socket 24 and/or interface 41 are discrete elements.

As described hereinabove, system 10 can be configured such that anchor head 30 is inaccessible to driver 40 (e.g., to anchor head 45 thereof). For some applications, interface 41 (or another component of crown 38) defines a floor 42, which separates driver 40 from anchor head 30 while the driver is seated within the interface. Alternatively or additionally, driver 40 (e.g., driver head 45 thereof) is shaped to define one or more shoulders 46 (e.g., positioned laterally, as shown in FIG. 1A). Often for such applications, shoulders 46 are dimensioned such that, while driver interface 41 is engaged by driver 40 (e.g., while driver head 45 is seated within the interface), the shoulders contact a proximal surface 29 of casing 20. Anchor head 30 being inaccessible to driver 40 facilitates transfer of torque from driver 40 to driver interface 41, while reducing (e.g., eliminating) direct transfer of a pushing force from the driver to anchor head 30, e.g., restricting any transfer of the pushing force to be via casing 20.

In some applications, and as shown, anchor 12 is transitionable between a first state (e.g., a torque-transfer state, FIG. 1B) and a second state (e.g., a non-torque-transfer state, FIG. 1C). In some applications, and as shown, while anchor 12 is in the first state, anchor head 30 is seated within socket 24. In this way, torque applied by driver 40 to driver interface 41 rotates socket 24, anchor head 30, and anchoring portion 34. In some applications, and as described hereinbelow, the first state facilitates screwing anchoring portion 34 into tissue 90.

Further in some applications and as shown, while anchor 12 is in the second state, anchor head 30 is disposed outside of (e.g., distally from) socket 24, such that torque applied by driver 40 to driver interface 41 rotates socket 24 relative to anchor head 30 (and thereby anchoring portion 34), e.g., such that torque is not transferred from the driver to the anchor head and the anchoring portion. Transition of anchor 12 from the first state to the second state occurs in response to anchor head 30 being pulled distally out of socket 24 by screwing of the anchor into tissue 90, e.g., as described hereinbelow in reference to FIGS. 2A-H.

For some applications, and as shown, anchor 12 further comprises a compression spring 26 that can be disposed between anchor head 30 and tissue-facing surface 28 (e.g., within casing 20). The function of spring 26 is described in more detail hereinbelow.

FIGS. 2A-H show driver 40 being used to screw anchoring portion 34 of anchor 12 into tissue 90 while anchor head 30 moves distally along longitudinal axis ax1, pressing surface 28 against the tissue. FIGS. 3A-H show corresponding steps, but with a variant 12' of anchor 12 that does not comprise compression spring 26. Henceforth, this variant of anchor 12 is referred to as anchor 12'.

FIG. 2A shows anchor 12 disposed against tissue 90, such that distal tissue-piercing point 36 contacts the tissue. Torque is then applied from driver head 45, via interface 41 and socket 24, to anchor 12, screwing anchoring portion 34 into tissue 90 (FIG. 2B). During this time, anchor 12 is in its torque-transfer state, and typically behaves similarly to a prior art tissue anchor of unitary construction. Thus, screwing of anchoring portion 34 into tissue 90 results in tissue-facing surface 28 moving distally along the longitudinal axis, until it contacts the tissue (FIG. 2C).

Figure 2H:
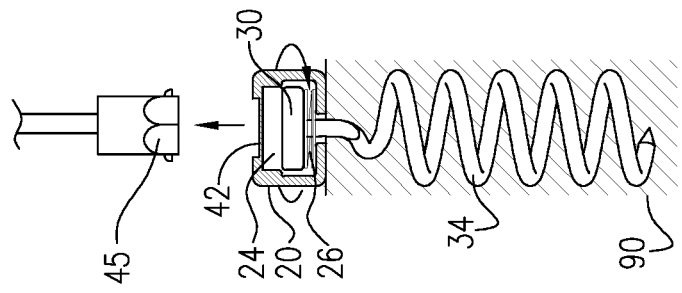
Figure 2G:
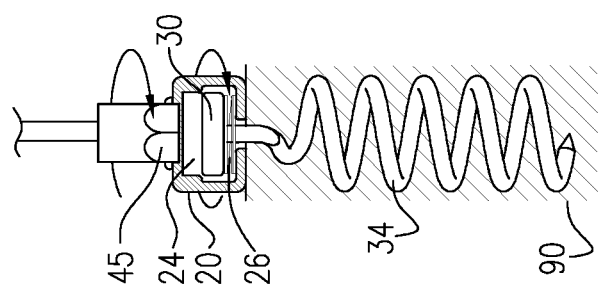
Figure 2F:
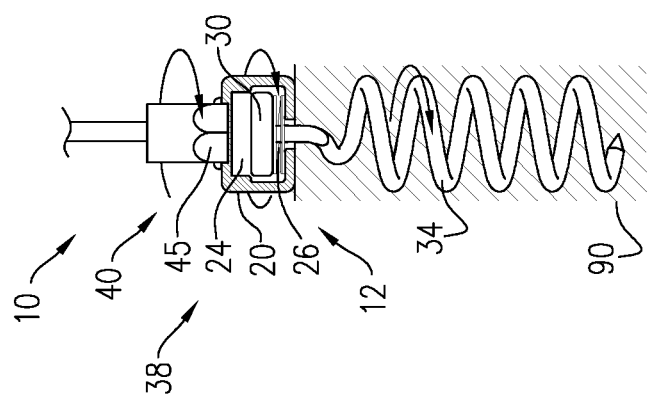

FIGS. 2D-F show further screwing of anchoring portion 34 into tissue 90, by continued rotation of driver head 45 and crown 38, despite anchoring portion 34 having already been screwed into tissue 90 sufficiently deep such that the tissue resists further distal movement of tissue-facing surface 28 and socket 24 (and often the entirety of casing 20). As shown in FIGS. 2D-F, this resistance contributes to the transition of the anchor from the first state to the second state, because once surface 28 has made contact with tissue 90 further screwing of anchoring portion 34 into the tissue progressively pulls anchor head 30 distally out of socket 24, which is inhibited by tissue 90 from advancing further distally. Since resistance from tissue 90 contributes to the transition of anchor 12 to the second state, torque applied to driver interface 41 is translated into distal motion of anchor head 30 relative to tissue-facing surface 28 (e.g., within casing 20), instead of being translated into application of a distal force by tissue-facing surface 28 to tissue 90. It is therefore hypothesized that triggering transition of anchor 12 from the first state to the second state, by tissue 90 resisting further distal movement of tissue-facing surface 28, may advantageously limit: (i) the distal force applied by the tissue-facing surface to the tissue while the anchor is screwed into the tissue, and/or (ii) a depth to which the tissue anchor can be screwed into the tissue.

In FIGS. 2D-E, anchor head 30 has moved further distally within casing 20, but has not yet completely exited socket 24 (e.g., the anchor head is partially disposed within the socket, and partially disposed within the free zone). Therefore, torque transfer to anchoring portion 34 is still possible. In FIG. 2F, anchor 12 has transitioned into its non-torque-transfer state, as anchor head 30 has been pulled completely out of socket 24 (i.e., into free zone 25), thereby rotationally disconnecting the socket from the anchor head. FIG. 2G illustrates that further rotation of driver head 45, rotates interface 41 and socket 24 (e.g., the entirety of casing 20), but does not result in further rotation of anchor head 30, or further screwing of anchoring portion 34 into the tissue. At this point in advancement of anchor 12 into tissue 90, torque applied by driver 40 to driver interface 41 rotates socket 24 relative to anchor head 30 and anchoring portion 34. It is therefore hypothesized that the transitioning of anchor 12 from the first state to the second state, in response to resistance from tissue 90 to tissue-facing surface 28, advantageously reduces a risk of overtightening or damaging the tissue contacted by tissue-facing surface 28.

At this point, the screwing of anchor 12 into tissue 90 is typically complete, and driver 40 can be removed (FIG. 2H).

As described briefly hereinabove, for some applications, and as shown, anchor 12 comprises compression spring 26 disposed within casing 20 (e.g., within free zone 25). For some such applications, spring 26 facilitates sustained screwing of anchor 12 into tissue 90 while the anchor transitions from the first state to the second state. Spring 26 can be disposed between anchor head 30 and tissue-facing surface 28. As anchor head 30 becomes progressively pulled out of from socket 24, and before the anchor head exits the socket entirely, the anchor head contacts spring 26 (FIG. 2E), such that further rotation of anchor head 30 begins to compress the spring, such that the spring presses tissue-facing surface 28 against tissue 90. It is hypothesized that, for some applications, spring 26 thereby advantageously increases reliability of anchor 12, by increasing a likelihood that tissue-facing surface 28 becomes pressed securely against tissue 90 before anchor 12 transitions into its non-torque-transfer state. To facilitate the described function of spring 26, while the spring is in a relaxed state (e.g., before anchor 12 has been introduced into the subject) an axial height 50 of anchor head 30 can be greater than an axial distance 52 between socket 24 (e.g., a distal end thereof) and spring 26. In the non-torque-transfer state of anchor 12, (e.g., once anchor 12 has been screwed into tissue 90), a combined axial height 54 of anchor head 30 and spring 26 can be similar to, but imperceptibly smaller than, an axial distance 56 between socket 24 (e.g., a distal end thereof) and a distal end of free zone 25. (Axial distance 56 can, for some applications, be considered the axial height of free zone 25.)

Figure 3H:
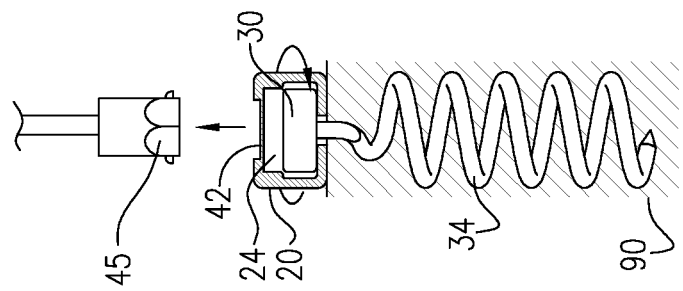
Figure 3G:
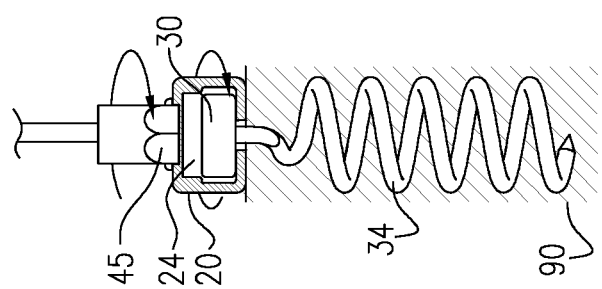
Figure 3F:
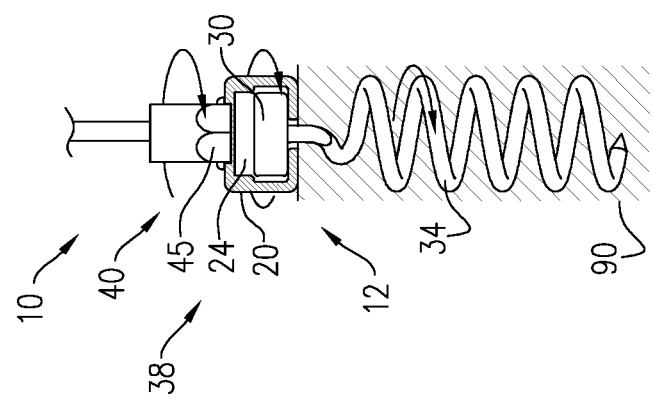
Figure 3E:
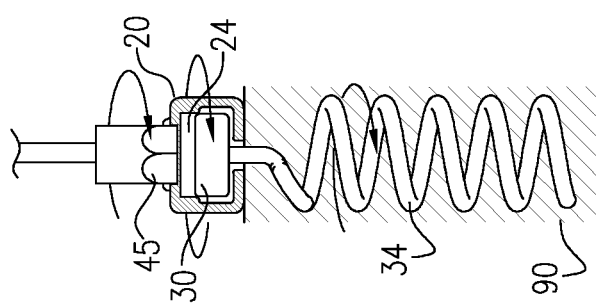

FIGS. 3A-H show the same sequence as FIGS. 2A-H, mutatis mutandis, but for the anchoring of anchor 12'. Anchor 12' is typically as described for anchor 12, except that anchor 12' lacks spring 26, and can be dimensioned differently in order to accommodate this lack of the spring. Anchor head 30 is typically dimensioned such that, upon the anchor head pressing tissue-facing surface 28 against tissue 90, the anchor head exits socket 24 (FIG. 3F), thereby transitioning anchor 12' into its non-torque-transfer state (FIG. 3G).

For some applications, to confer reliability on anchor 12', e.g., to reduce a likelihood that anchor 12' transitions into its non-torque-transfer state before its tissue-facing surface 28 becomes pressed securely against tissue 90, an axial height 58 of anchor head 30 can be similar to, but imperceptibly smaller than, axial distance 56.

Reference is made to FIGS. 4A-D, 5A-E, and 6A-B, which are schematic illustrations showing an example tissue anchor system 110, in accordance with some applications. Reference is also made to FIGS. 7A-C, 8A-E, and 9A-C, which are schematic illustrations showing an example tissue anchor system 210, in accordance with some applications.

Systems 10, 110 and 210 have several features in common with each other. Furthermore, components that are identically named between the systems typically share similar features and serve similar functions as each other. For example, each of tissue anchors 112 and 212 comprises a driver interface 141, 241 shown being engaged by driver head 45 and rotated using driver 40. As such, the description below of systems 110 and 210 focuses upon features that distinguish each system from system 10.

Systems 110 and 210 are described as comprising anchor driver 40 (described hereinabove in reference to FIGS. 2 and 3A-H), but each of these systems can optionally comprise a different anchor driver.

Figure 4A:
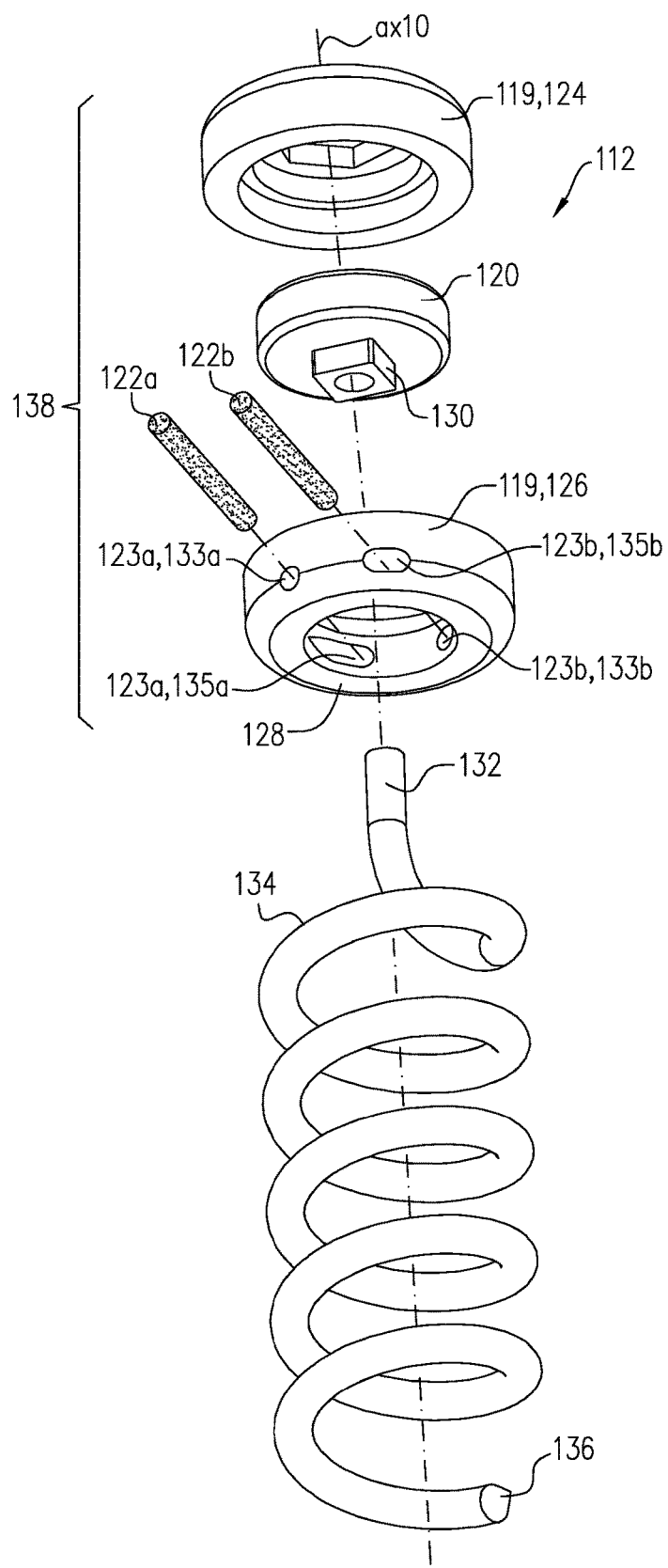
FIGS. 4A-D, 5A-E and 6A-B are schematic illustrations showing an example tissue anchor system, in accordance with some applications.

For some applications, and as shown in FIGS. 4A and 7A, each crown 138, 238 comprises a respective housing 119, 219 which comprises a proximal casing 124, 224 and a distal casing 126, 226. A plurality of grooves 123, 223 (e.g., grooves 123a and 123b, or grooves 223a and 223b, respectively) are shown as being defined by distal casing 126, 226 yet the grooves can optionally be defined by proximal casing 124, mutatis mutandis.

Each crowns 138, 238 respectively comprises an anchor head 130 or gear 230 that is fixedly coupled via a neck 132, 232 to an anchoring portion 134, 234, having a distal tissue-piercing point 136, 236, such that rotation of the anchor head or gear rotates the anchoring portion about a longitudinal axis ax10, ax20, as described hereinabove in reference to anchor 12.

Crowns 138 and 238 of tissue anchors 112 and 212 do not utilize a socket in the manner described for crown 38 of anchor 12. Instead, each of crowns 138 and 238 comprises elements that function together as a slip clutch 140, 240 that couples (e.g., selectively rotatably couples) their respective driver interface 141, 241 to the respective anchor head 130 or gear 230 of crowns 138, 238.

Selective rotational coupling of interface 141, 241 to anchor head 130 or gear 230 by way of slip clutch 140, 240 facilitates transfer of torque from the driver interface to the anchor head, yet limits the transferred torque such that the torque does not exceed a torque threshold. It is hypothesized that using a slip clutch to limit the transferred torque reduces a risk of overtightening the anchor or damaging the tissue. It is further hypothesized that, for some applications, using a slip clutch in this manner may also reduce a risk of under-tightening the anchor, by enabling a surgeon to confidently tighten the anchor without inadvertently overtightening.

Figure 4B:
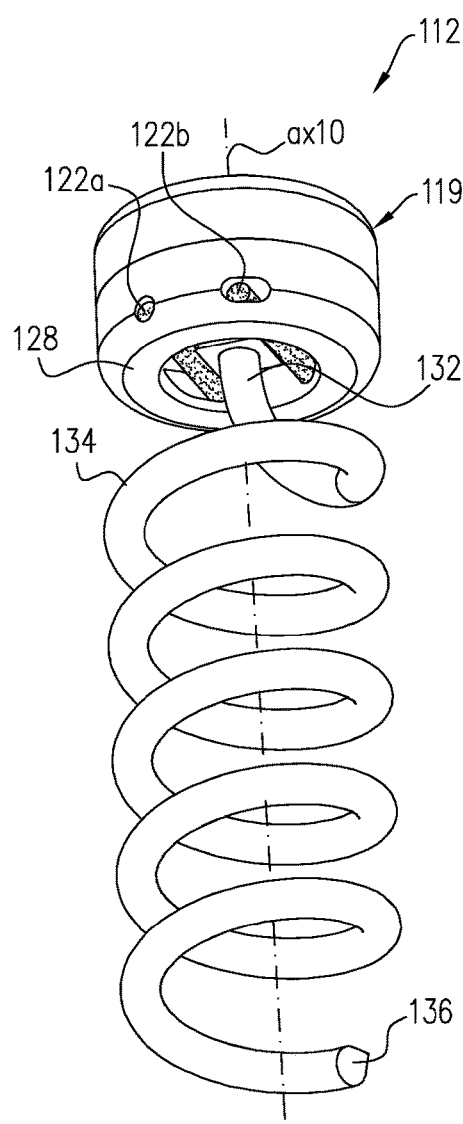
Figure 4C:
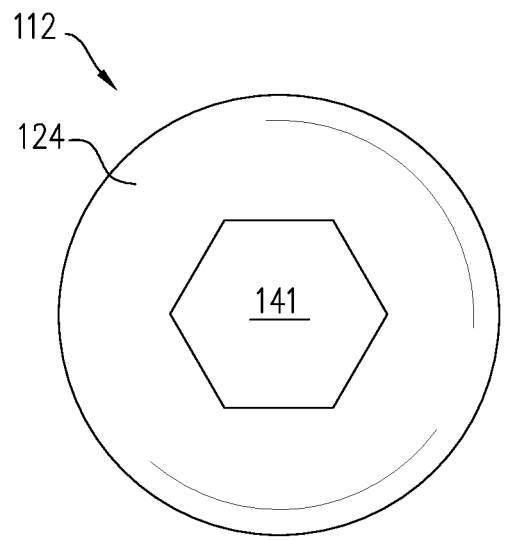
Figure 4D:
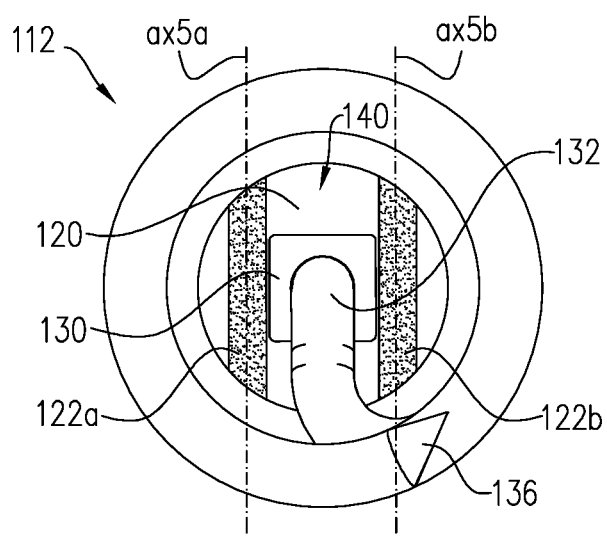
Figure 5A:
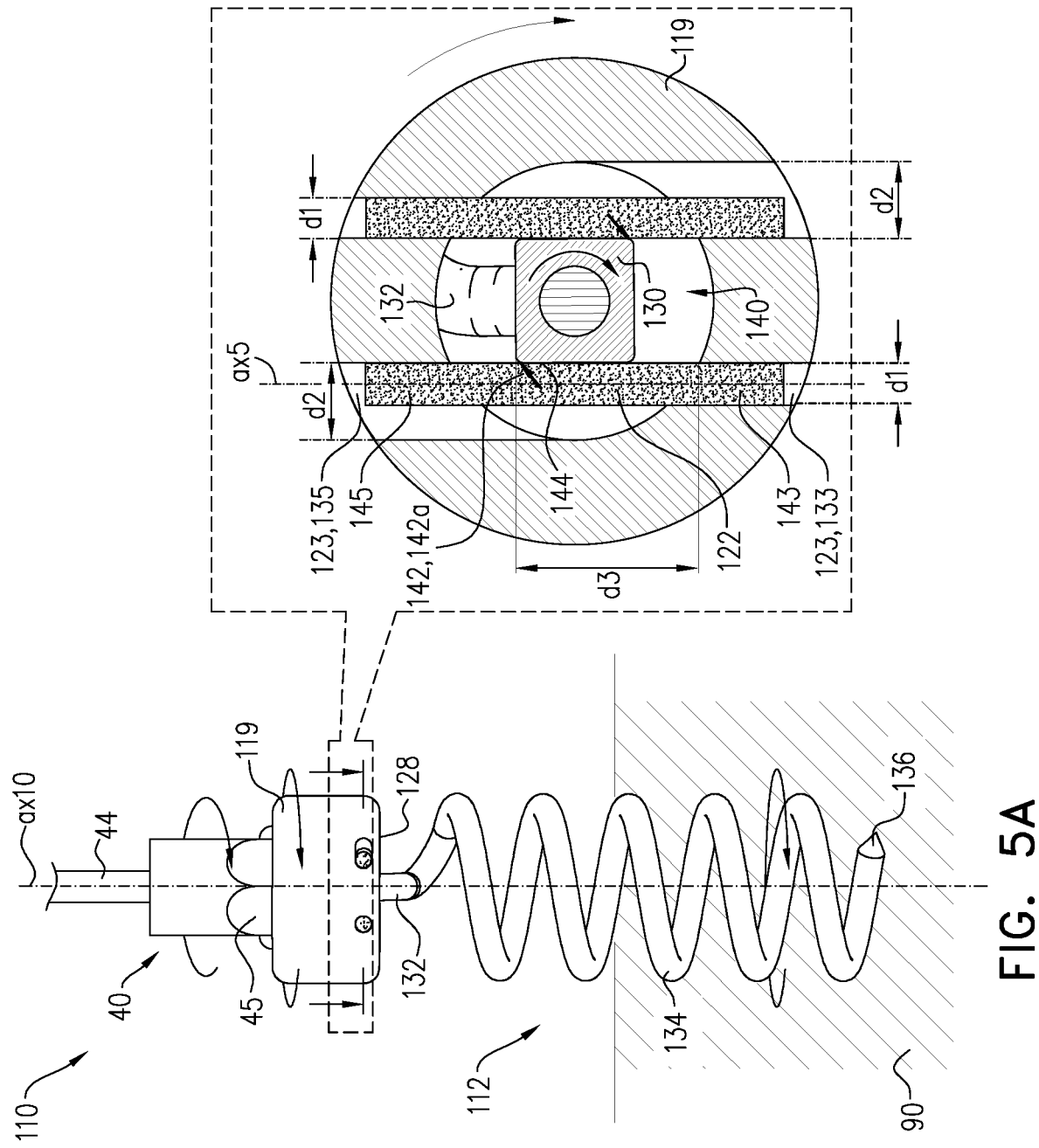

As shown in FIGS. 4A-D, slip clutch 140 defined by crown 138 of tissue anchor 112 comprises one or more cantilever pins 122 disposed along a respective groove axis ax5 (e.g., a first cantilever pin 122a disposed along a first groove axis ax5a, and a second cantilever pin 122b disposed along a second groove axis ax5b), such that each pin is disposed within a respective groove 123 defined by housing 119. As shown in FIG. 5A, groove 123 comprises a loose portion 135, within which a free portion 145 of pin 122 is disposed, and a tight portion 133 within which a fixed portion 143 of the pin is disposed (e.g., such that the fixed portion is fixedly coupled to driver interface 141). A loose-portion width d2 of the loose portion can be greater than a tight-portion width d1 of the tight portion.

In some applications, and as shown in FIG. 5A, each groove axis ax5 lies on a groove plane that is generally perpendicular to longitudinal axis ax1 and longitudinally aligned with anchor head 130. In this way, each of pins 122 is longitudinally aligned with anchor head 130. In transverse cross-section (e.g., FIG. 5A), anchor head 130 has a non-circular profile, defining a plurality of lateral surfaces (e.g., sides) 144. Although anchor head 130 is shown as having a square profile, this is not meant to exclude other shapes (e.g., other polygons, such as a hexagon). In a resting state of anchor 112 (e.g., as shown in FIGS. 4B and 4D), each of pins 122 is in contact with a lateral surface 144 of anchor head 130.

In some applications, and as shown, anchor head 130 is coupled to a bearing 120 that is housed within housing 119 such that the bearing is rotationally coupled to the housing, and rotationally couples the anchor head and anchoring portion 134 to the housing. In some applications, bearing 120 is housed snugly within housing 119 so as to provide smooth rotation with little wobble. In this way, rotation of driver interface 141 rotates housing 119, yet whether rotation of the housing will rotate bearing 120, anchor head 130 and anchoring portion 134, is dependent upon contact between cantilever pins 122 (e.g., lateral surface 144 thereof) and the anchor head—i.e., on slip clutch 140.

In some applications, rotational coupling of driver interface 141 to anchor head 130 is accomplished via contact between cantilever pins 122 and the anchor head, e.g., by the cantilever pins pressing against lateral surfaces 144 of the anchor head. For example, and as described in more detail hereinbelow, the system can be configured such that application, to interface 141, of torque below the torque threshold, rotates the housing 119, pins 122 and anchor head 130 in unison, while the pins remain in contact with lateral surfaces 144 of the anchor head. However, application of torque above the torque threshold will typically cause the anchor head to push against the pins, such that the pins deflect laterally away from longitudinal axis ax10, while the pins (and housing 119) revolve around the anchor head. In this way, torque exceeding the torque threshold may not be transferred to anchor head 130.

For some applications, and as shown in FIG. 5A, torque is transferred to lateral surface 144 of anchor head 130, from a portion of pins 122, e.g., from a torque-applying portion 142 (e.g., a first torque-applying portion 142a), between fixed portion 143 and free portion 145—that is in contact with the lateral surface of the anchor head. For some such applications, while screwing anchoring portion 134 into tissue 90, torque-applying portion 142 comprises a leading end of pin 122, such that the torque-applying portion revolves ahead of fixed portion 143 while pin 122 revolves about axis ax10.

For some applications, and as shown, torque-applying portion 142 is defined merely by virtue of being the portion of pin 122 via which torque is applied to anchor head 130, rather than being a physical or other distinguishing feature of that portion of the pin.

The rotational arrows in FIG. 5A indicate that torque applied to driver interface 141, using driver 40, causes housing 119, anchor head 130 and anchoring portion 134 to rotate with pins 122, thereby facilitating screwing the anchor 112 into tissue 90.

Figure 5B:
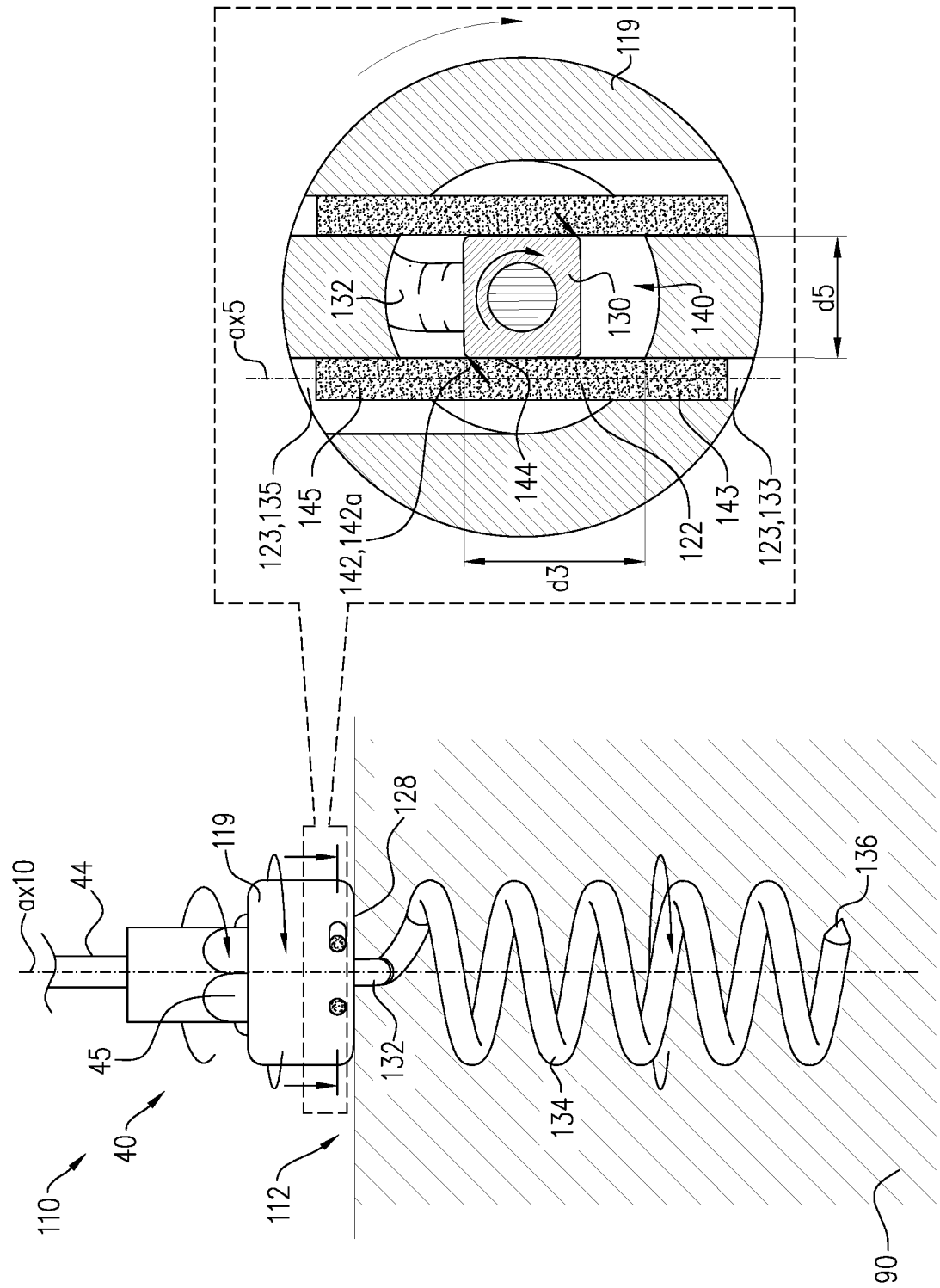

FIG. 5B shows anchor 112 having been screwed into tissue 90, due to continued application of torque, to anchor interface 141, in the first direction (e.g., forward torque applied in a forward direction). Screwing anchor 112 into tissue 90 has moved the anchor distally, such that a tissue-facing surface 128 contacts the tissue. At this point, resistance provided by the tissue to further distal movement of tissue-facing surface 128 increases the magnitude of torque required to continue to rotate driver interface 141 above the torque threshold (e.g., increasing the required torque from a first magnitude that is below the torque threshold, to a second magnitude that is above the torque threshold).

Figure 5C:
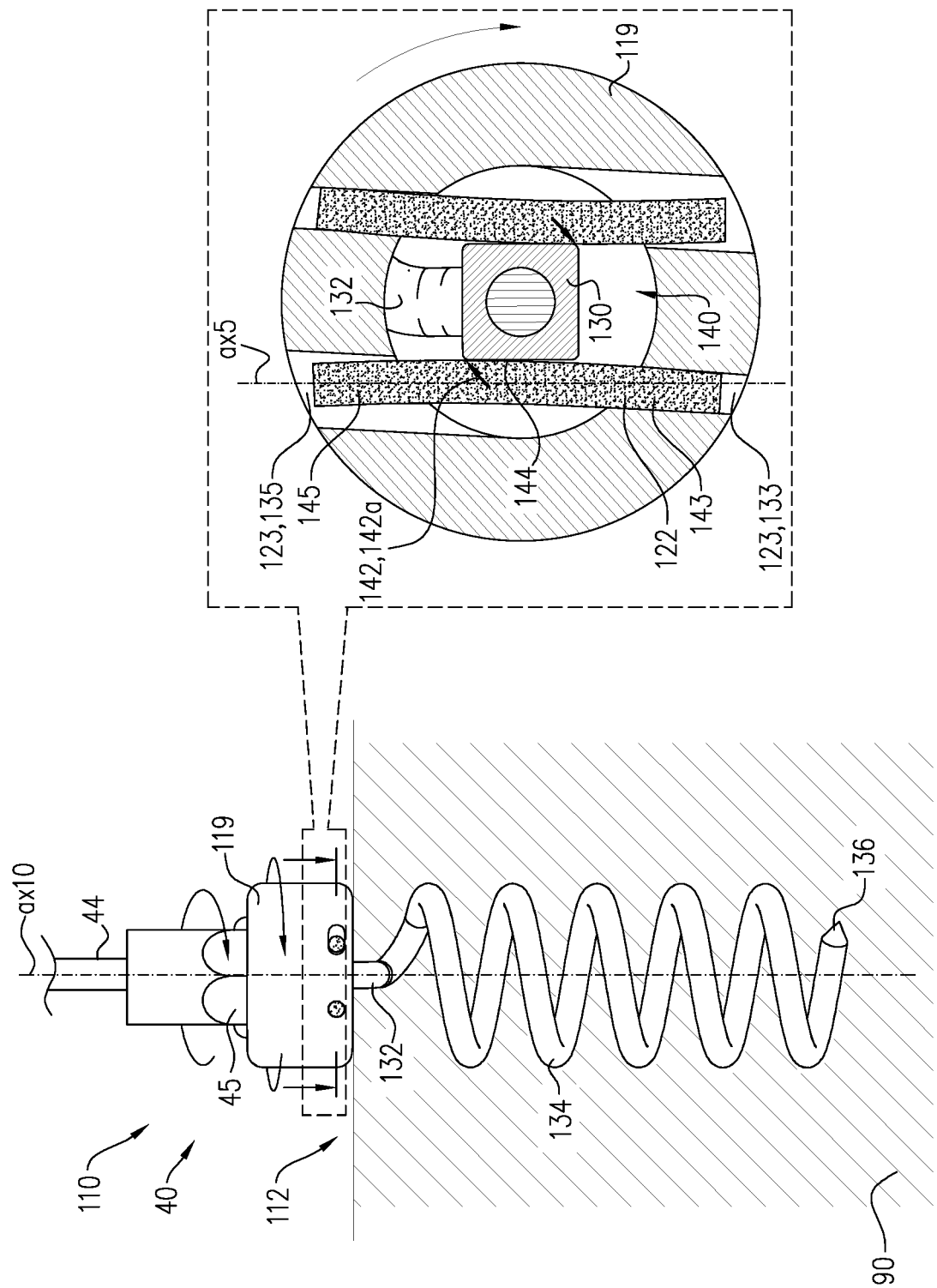

As shown in FIG. 5C, anchor head 130 (e.g., lateral surface 144 thereof) begins to deflect pin 122 away from longitudinal axis ax10, such that the pins are not entirely parallel to groove axis ax5, and slip clutch 140 begins to slip.

In some applications, pins 122 are sufficiently flexible to deflect, while torque is applied to interface 141 at above the torque threshold, and torque-applying portion 142a contacts anchor head 130 at one end of a cantilever span (e.g., a forward cantilever span d3), while fixed portion 143 of the pin is fitted within tight portion 133 at another end of the cantilever span. Thus, the forward cantilever span is typically measured along the pin from (i) torque-applying portion 142a, to (ii) fixed portion 143. Flexibility of pin 122 and/or a length of forward cantilever span d3 can be configured in order to set the torque threshold of slip clutch 140.

Figure 5D:
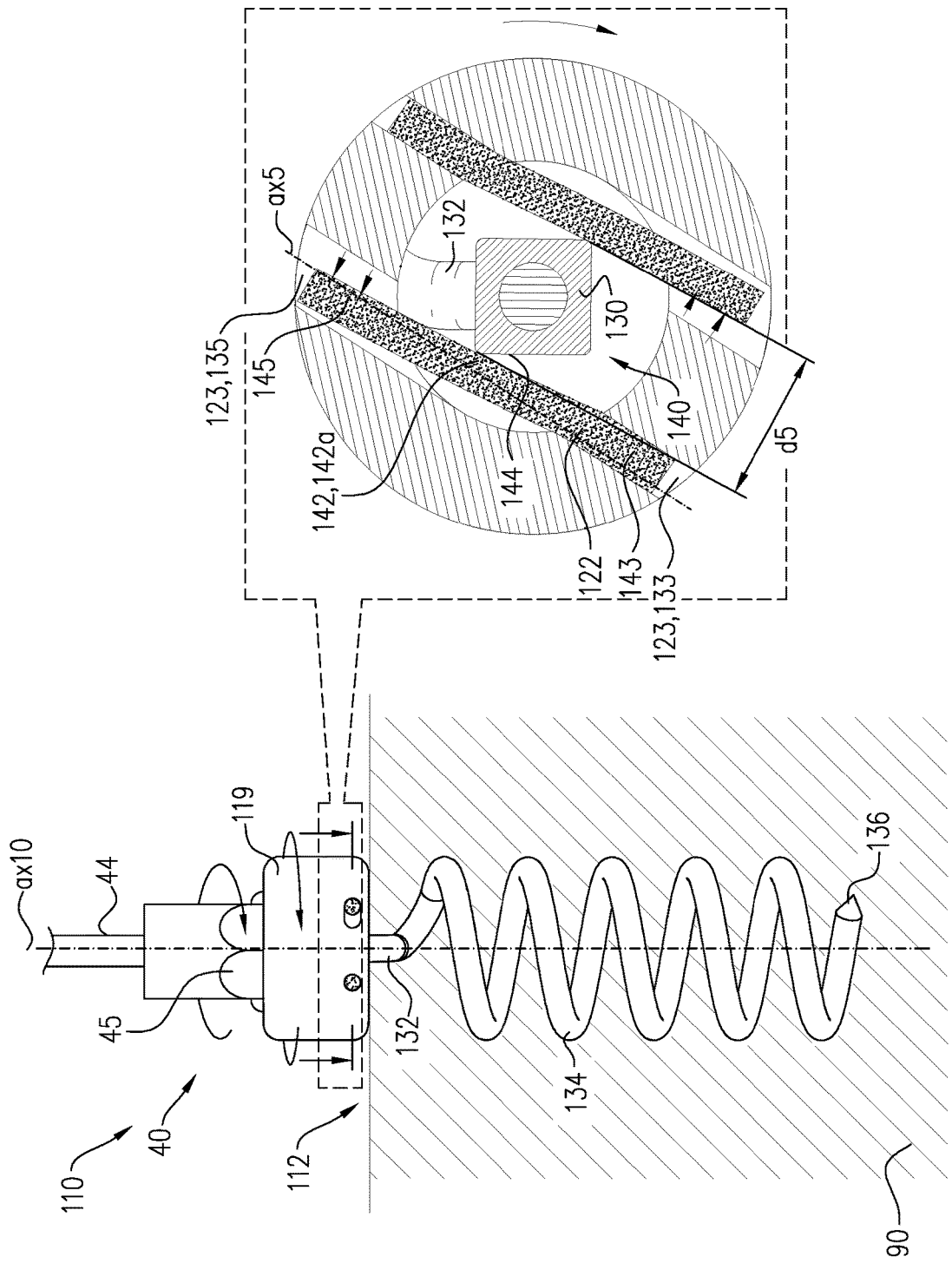

FIG. 5D shows slip clutch 140 having continued to slip, such that pins 122 have deflected further away from longitudinal axis ax1, and an inter-pin distance d5 between points of contact of respective pins 122 with anchor head has increased, as free portions 145 of the pins pivot within loose portions 135 of grooves 123. At this stage, pins 122 have begun to slip (i.e., revolve) around anchor head 130, such that continued application of torque at the second magnitude causes driver interface 141 to rotate with respect to the anchor head and anchoring portion 134—i.e., to rotate without further screwing of the anchoring portion into the tissue.

Figure 5E:
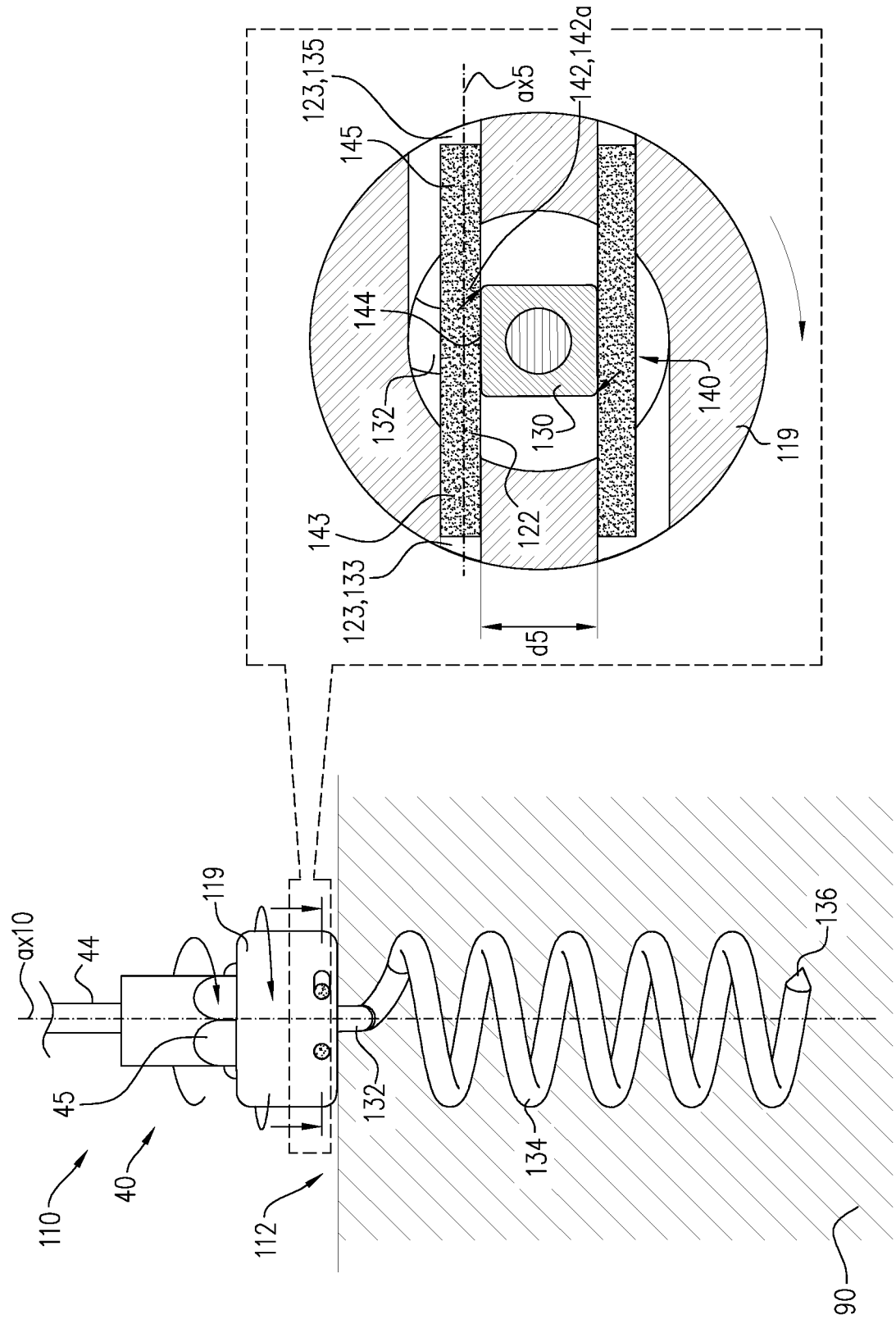

As shown in FIG. 5E, further rotation of interface 141 allows pins 122 to deflect medially toward their original conformation, and inter-pin distance d5 is reduced, as the interface and the pins complete a quarter turn since their orientation shown in FIG. 5B.

In certain situations, it may be desirable to remove tissue anchor 112 from tissue 90 (e.g., after having partially or fully screwed the tissue anchor into the tissue). For instance, the surgeon may choose to move the anchor (e.g., to an alternate portion of an implant, and/or to an alternate location of tissue), or to remove the anchor entirely (e.g., due to the anchor no longer being necessary).

Figure 6A:
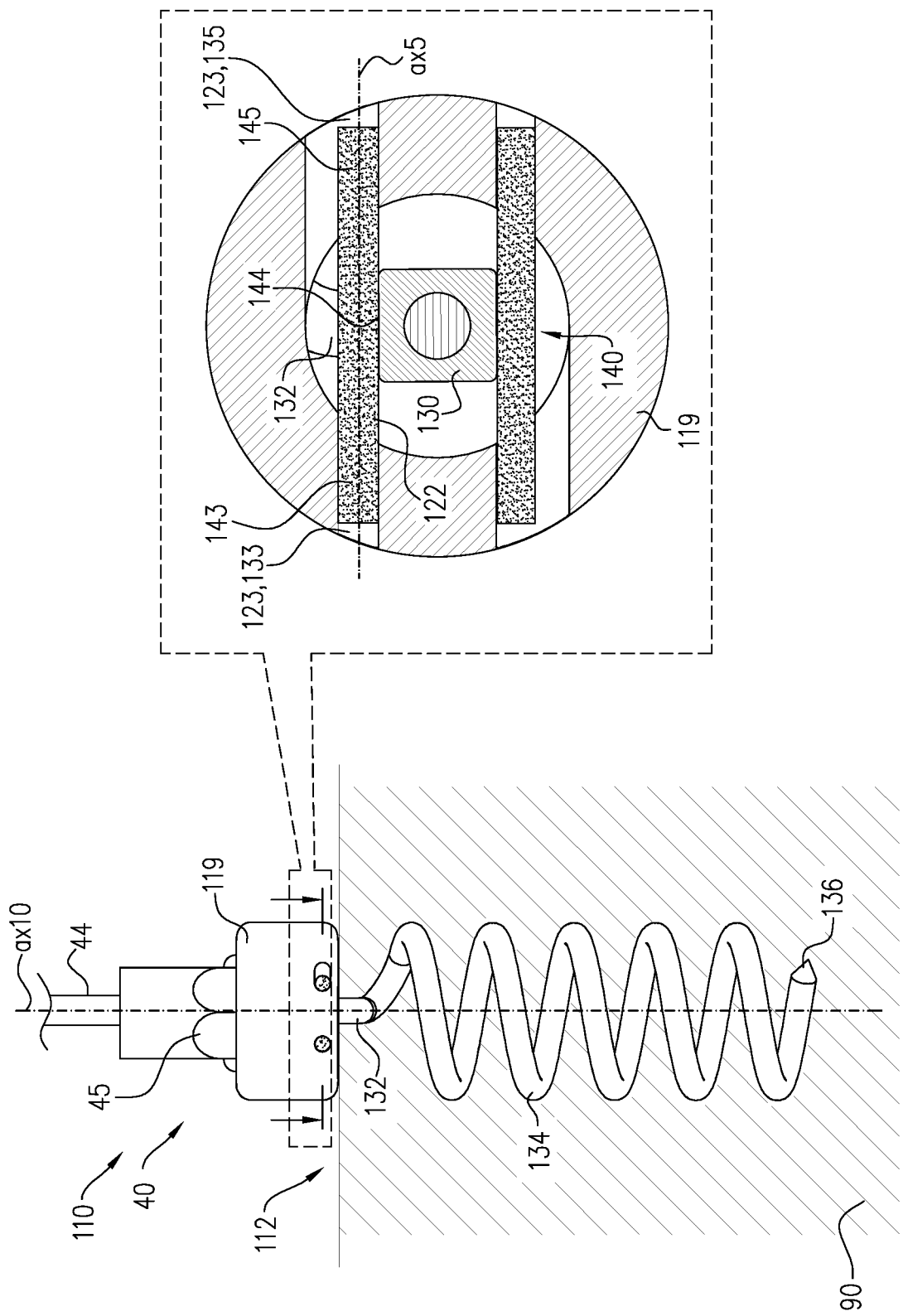
Figure 6B:
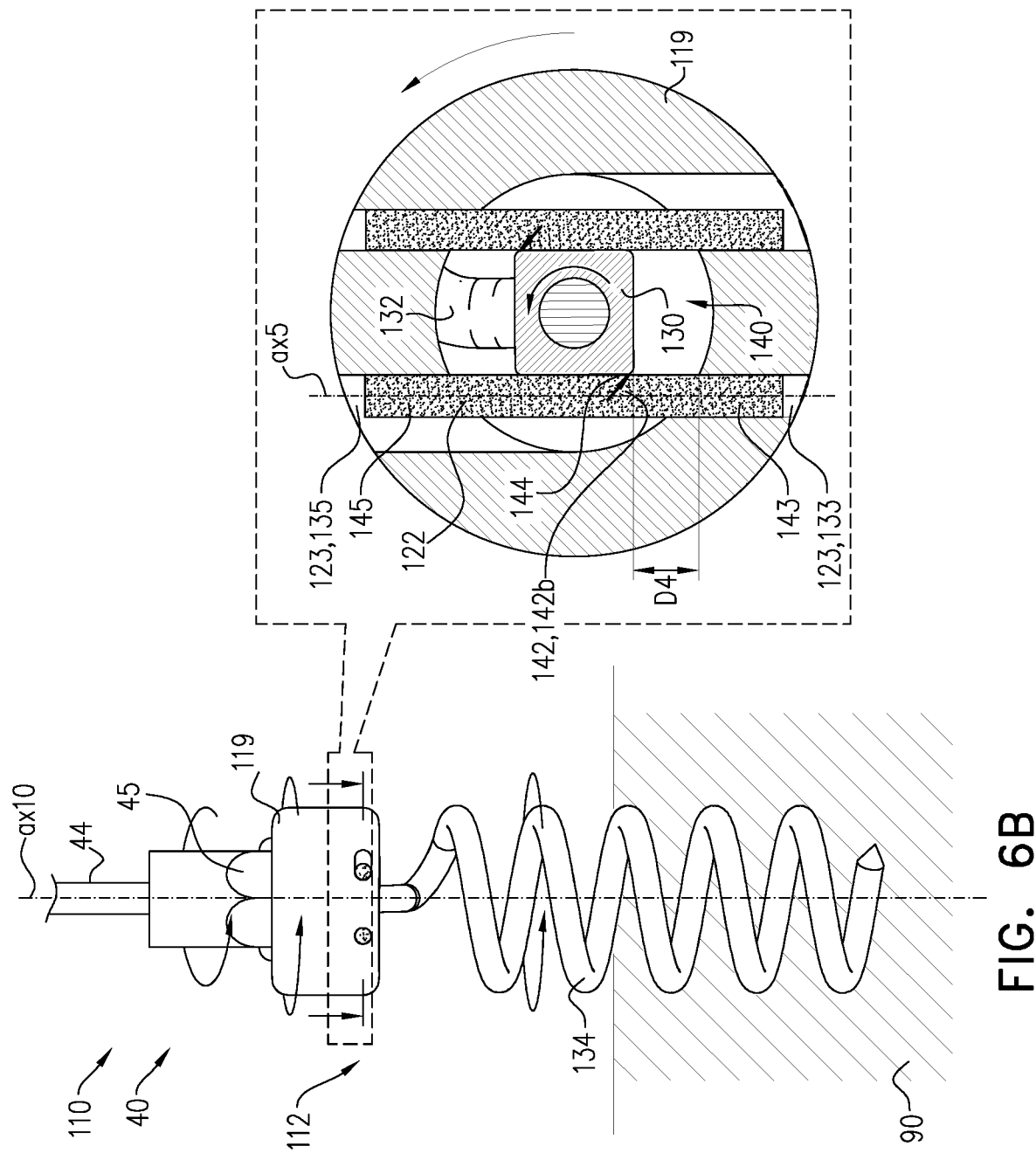

As shown in FIGS. 6A-B, removal of anchor 112 from tissue 90 is accomplished by applying reverse torque (i.e., torque in a second rotational direction that is opposite to the first rotational direction) to interface 141, such that pins 122 revolve about longitudinal axis ax10 in the second rotational direction, while the pins contact lateral surface 144 of the anchor head.

For some applications, it may be important to ensure that sufficient reverse torque can be applied to unscrew the anchor, despite the original anchoring torque having been limited. Furthermore, in some cases, the surgeon may encounter greater resistance to unscrewing anchor 121, than that encountered when initially screwing the anchor into tissue 90. For instance, development of scar tissue at an implantation site of anchor 121 may impede removal of the anchor. In order to facilitate unscrewing of anchor 112 from tissue 90, some applications of tissue anchor 112 allow more reverse torque than forward torque to be transferred from driver interface 141 to anchor head 130.

Therefore, for some such applications, reverse torque exceeding the torque threshold (e.g., at the second magnitude) can be transferred from driver interface 141 to anchor head 130. That is, pins 122 are sufficiently rigid to resist deflection while reverse torque is applied at the second magnitude to interface 141, and torque-applying portion 142b contacts anchor head 130 at one end of reverse cantilever span d4, while fixed portion 143 of the pin is fitted within tight portion 133 at another end of the reverse cantilever span. For some such applications, while unscrewing anchoring portion 134 from tissue 90, torque-applying portion 142 comprises a leading end of pin 122, such that the torque-applying portion revolves ahead of fixed portion 143 while the pin revolves about axis ax10.

As shown, the reverse cantilever span is typically measured along the pin from (i) torque-applying portion 142b, to (ii) fixed portion 143. Reverse cantilever span d4 is typically shorter than forward cantilever span d3, such that torque-applying portion 142b is closer to fixed portion 143 when unscrewing anchor 112, than torque-applying portion 142a is to fixed portion 143 when screwing the anchor into tissue 90. It is hypothesized that a magnitude of torque that can be applied, via pin 122, from anchor interface 141 to anchor head 130, is inversely related to the length of the cantilever span, such that a greater magnitude of torque can be transferred along a shorter cantilever span.

However, it may be desirable to limit also the magnitude of reverse torque that can be applied. Therefore, for some applications, slip clutch 140 limits the magnitude of reverse torque that can be applied from interface 141 to anchor head 130 while unscrewing tissue anchor 112. For such applications, a second torque threshold (i.e., a reverse torque threshold), greater than the first torque threshold, is typically established. Thereby, application of torque at a third magnitude, exceeding the second torque threshold, may cause slip clutch 140 to slip, and driver interface 141 to rotate with respect to anchor head 130 and anchoring portion 134.

Reference is made again to FIGS. 7A-C, 8A-E, and 9A-C, which show tissue anchor 212 of system 210. As described hereinabove, tissue anchor 212 shares features with tissue anchor 112. As such, the description hereinbelow focuses upon features that distinguish anchor 212 from anchor 112, particularly features of slip clutch 240 which differ from those of slip clutch 140. For example, slip clutch 240 comprises a gear 230 in place of anchor head 130, and a cantilever pin 222 in place of pin 122. Slip clutch 240 is therefore a ratcheting slip clutch in which pin 222 defines a pawl that interacts with gear 230 as described in greater detail hereinbelow.

Similarly to slip clutch 140, slip clutch 240 facilitates transfer of torque from the driver interface to the anchor head, yet limits the magnitude of torque that can be applied when screwing tissue anchor 212 into tissue 90, by selectively rotationally coupling driver interface 241 to gear 230.

Grooves 223 are dimensioned to snugly fit pins 222, similarly to way that tight portions 133 fit pins 122, and pins 222 are typically dimensioned such that while fixed portions 243 thereof are disposed within grooves 223, the pins (e.g., torque-applying portions 242 thereof) are in contact with gear 230 (e.g., a non-circular lateral surface 244 thereof). In a resting state of anchor 212 (e.g., as shown in FIGS. 7B and 7C), each of pins 222 is in contact with lateral surface 244 of gear 230.

For some applications, and similarly to as described hereinabove in reference to anchor head 130 of system 110, gear 230 is coupled to a bearing 220 that is housed within housing 219 such that the bearing is rotationally coupled to the housing, and rotationally couples the gear and anchoring portion 234 to the housing. For some applications, bearing 220 is housed snugly within housing 219 so as to provide smooth rotation with little wobble. In this way, rotation of driver interface 241 rotates housing 219, yet whether rotation of the housing will rotate bearing 220, gear 230 and anchoring portion 234, is dependent upon contact between pins 222 (e.g., lateral surface 244 thereof) and the gear.

Figure 8A:
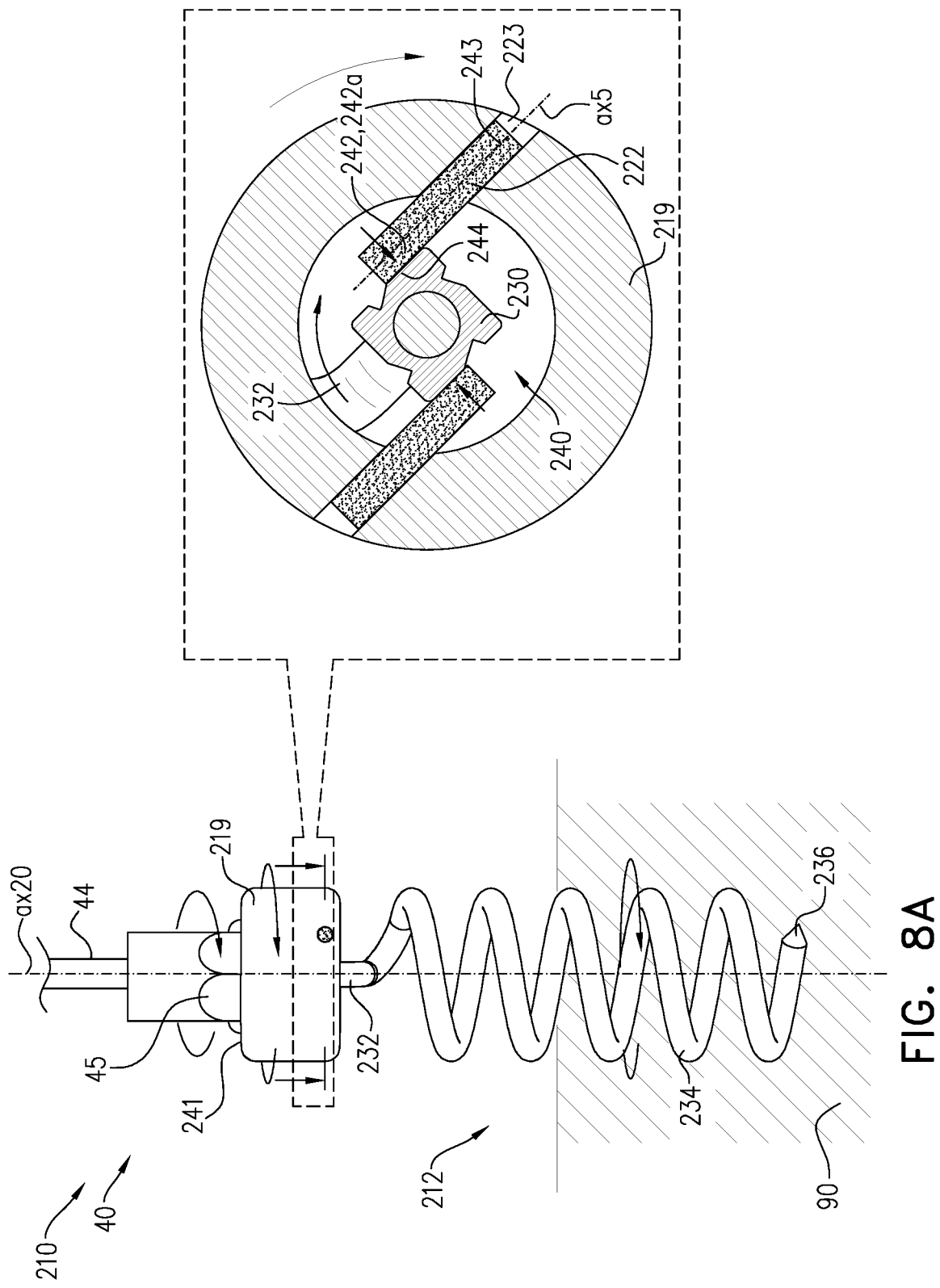

FIG. 8A shows anchor 212 being screwed into tissue 90. The rotational arrows in FIG. 8A indicate that torque applied to driver interface 241, using driver 40, causes housing 219, gear 230 and anchoring portion 234 to rotate, thereby screwing anchoring portion 234 into tissue 90. Similarly to as described hereinabove in reference to slip clutch 140, while torque is applied to interface 241 at under the torque threshold, pins 222 revolve about longitudinal axis ax20 while torque-applying portions 242a of the pins are in contact with lateral surface 244 of gear 230, causing the gear and anchoring portion 234 to rotate. However, in contrast that described hereinabove with reference to slip clutch 140, while screwing anchoring portion 234 into tissue 90, fixed portion 243 comprises a leading end of pin 222, such that the fixed portion revolves ahead of torque-applying portion 242 while the pin revolves about axis ax20.

Figure 8B:
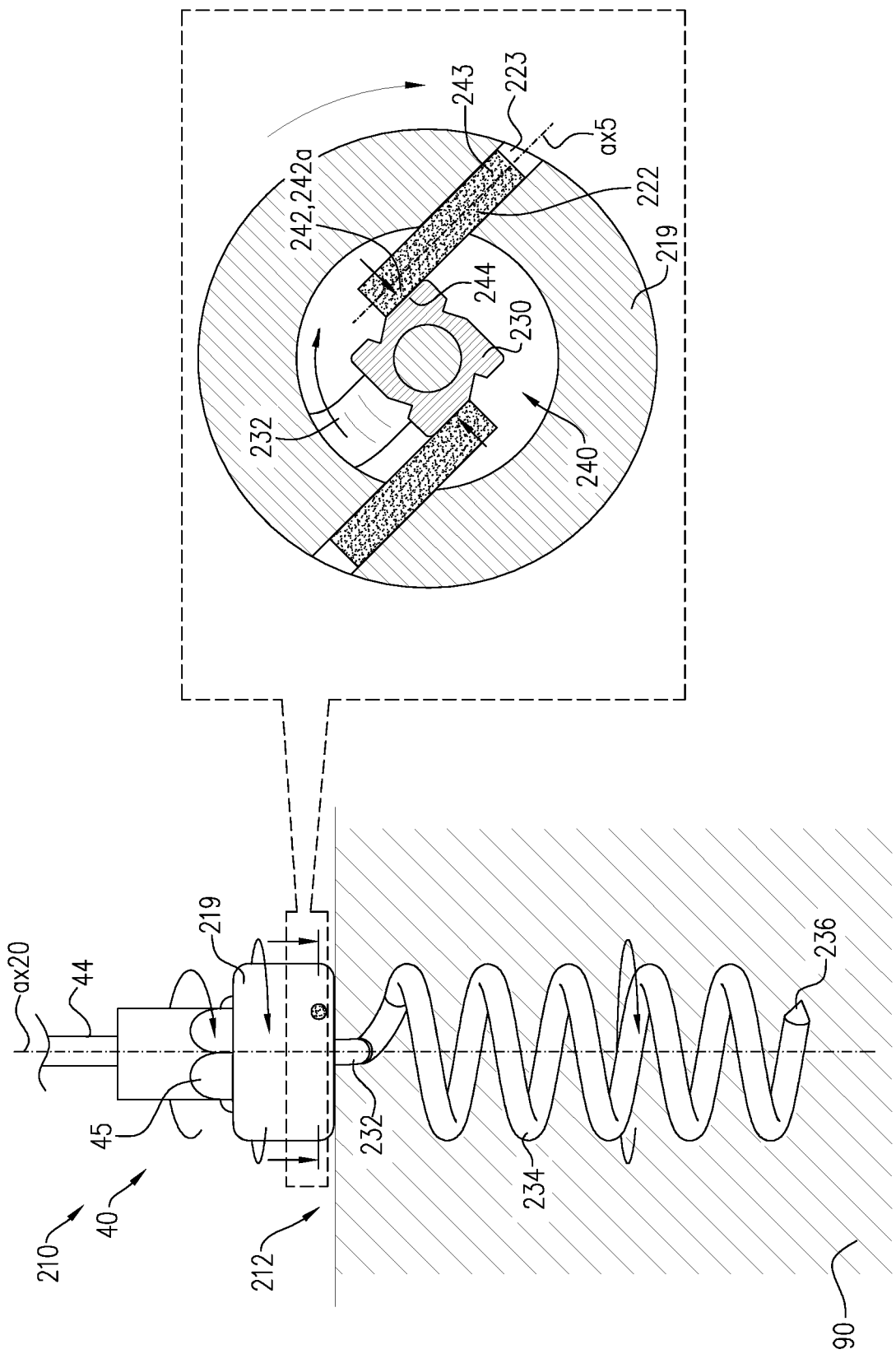

FIG. 8B shows anchor 212 having been screwed into tissue 90, due to continued application of forward torque to anchor interface 241. Screwing anchor 212 into tissue 90 has moved the anchor distally, such that a tissue-facing surface 228 contacts the tissue. As described hereinabove in reference to tissue anchor 121, resistance provided by the tissue to further distal movement of tissue-facing surface 228 increases the magnitude of torque required to rotate driver interface 241 (e.g., from the first magnitude to the second magnitude) to beyond the torque threshold.

Figure 8C:
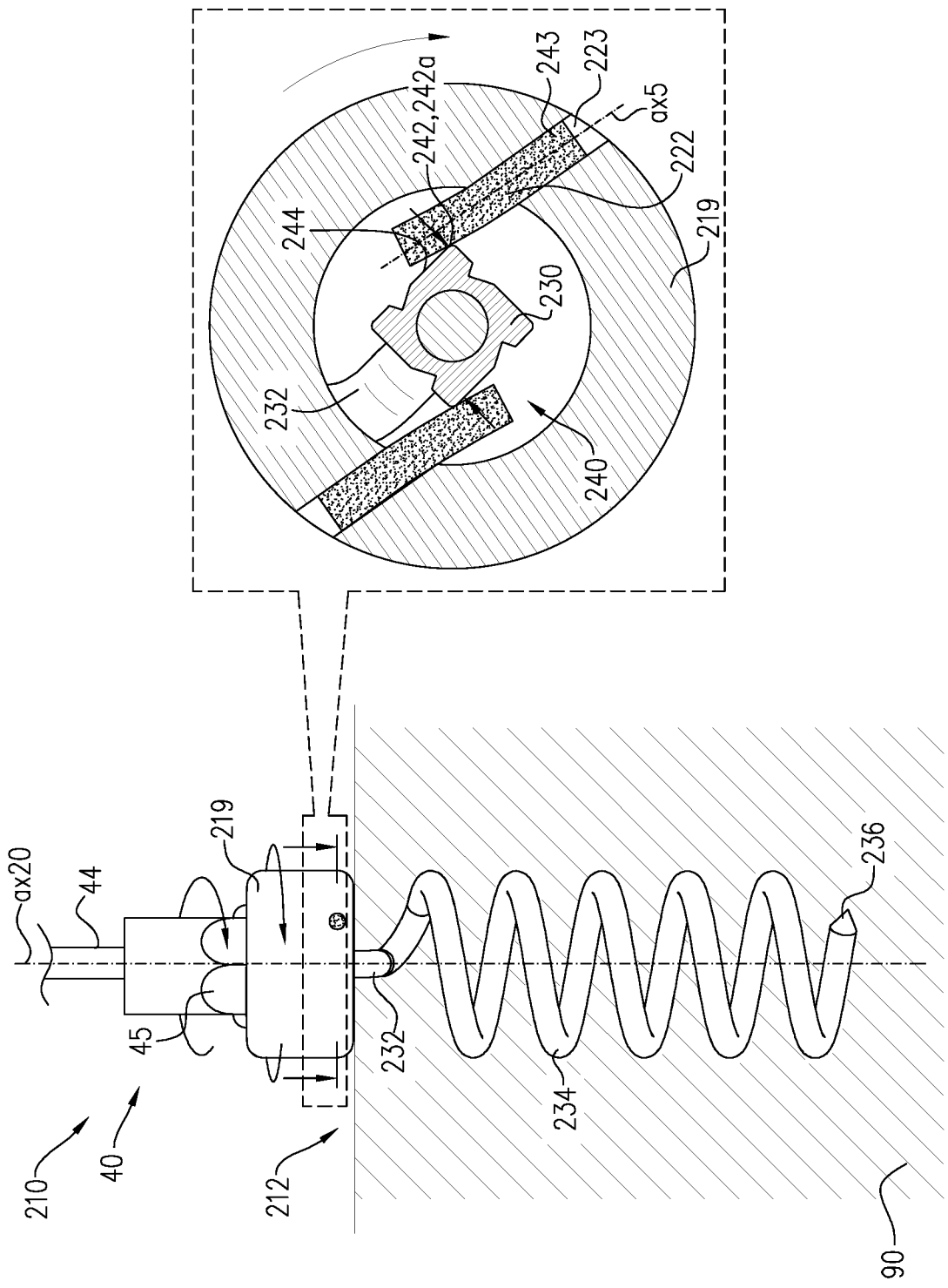
Figure 8D:
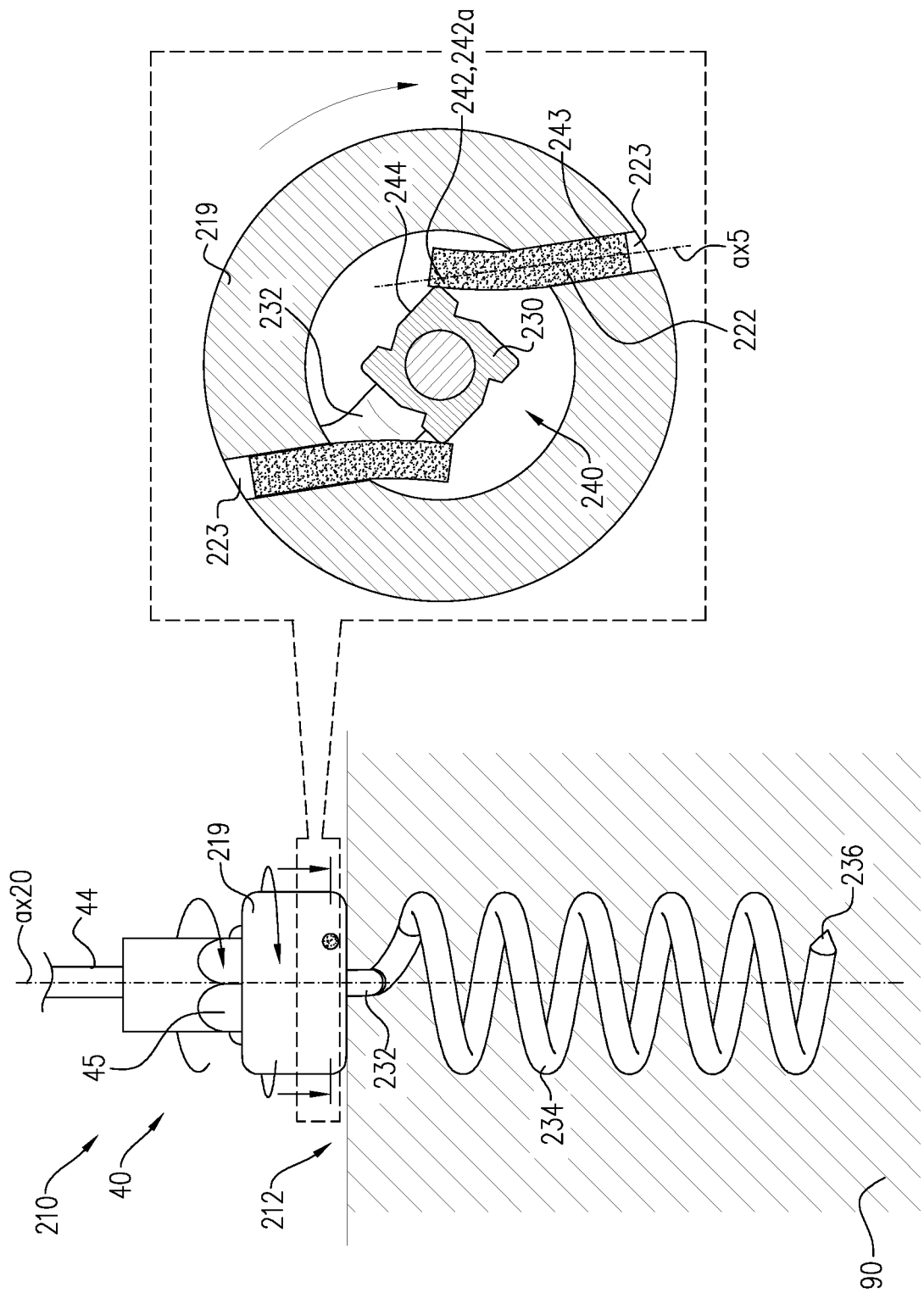

As shown in FIG. 8C, gear 230 (e.g., lateral surface 244 thereof) begins to deflect torque-applying portions 242a of pins 222 laterally away from longitudinal axis ax20, such that the pins are not entirely parallel to axis ax5. Pins 222 begin to slip around gear 230, thereby reducing the torque transferred from driver interface 241 to gear 230. FIG. 8D shows gear 230 having further deflected pins 222 (e.g., torque-applying portions 242a thereof) away from longitudinal axis ax20, such that slip clutch 240 has continued to slip around gear 230. At this stage, application of forward torque at the second magnitude causes driver interface 241 and pins 222 to rotate with respect to gear 230 and anchoring portion 234.

Figure 8E:
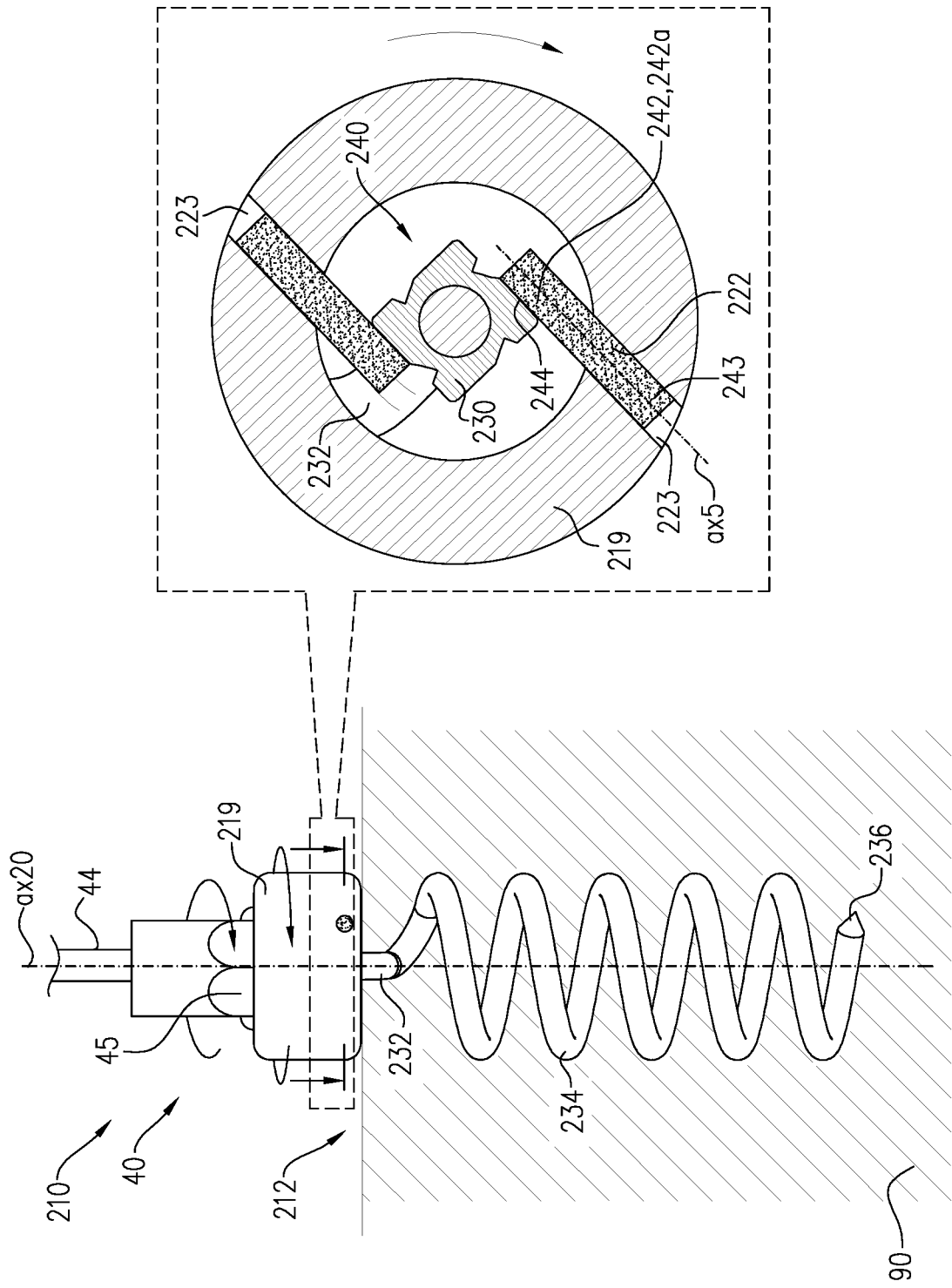

As shown in FIG. 8E, further rotation of interface 241 allows pins 222 to deflect medially toward their original conformation, as the interface and the pins complete a quarter turn since their orientation shown in FIG. 8B.

Similarly to as described hereinabove regarding tissue anchor 112 with reference to FIGS. 6A-B, it may be desirable in certain situations to remove tissue anchor 212 from tissue 90 (e.g., after having partially or fully screwed the tissue anchor into the tissue).

Figure 9A:
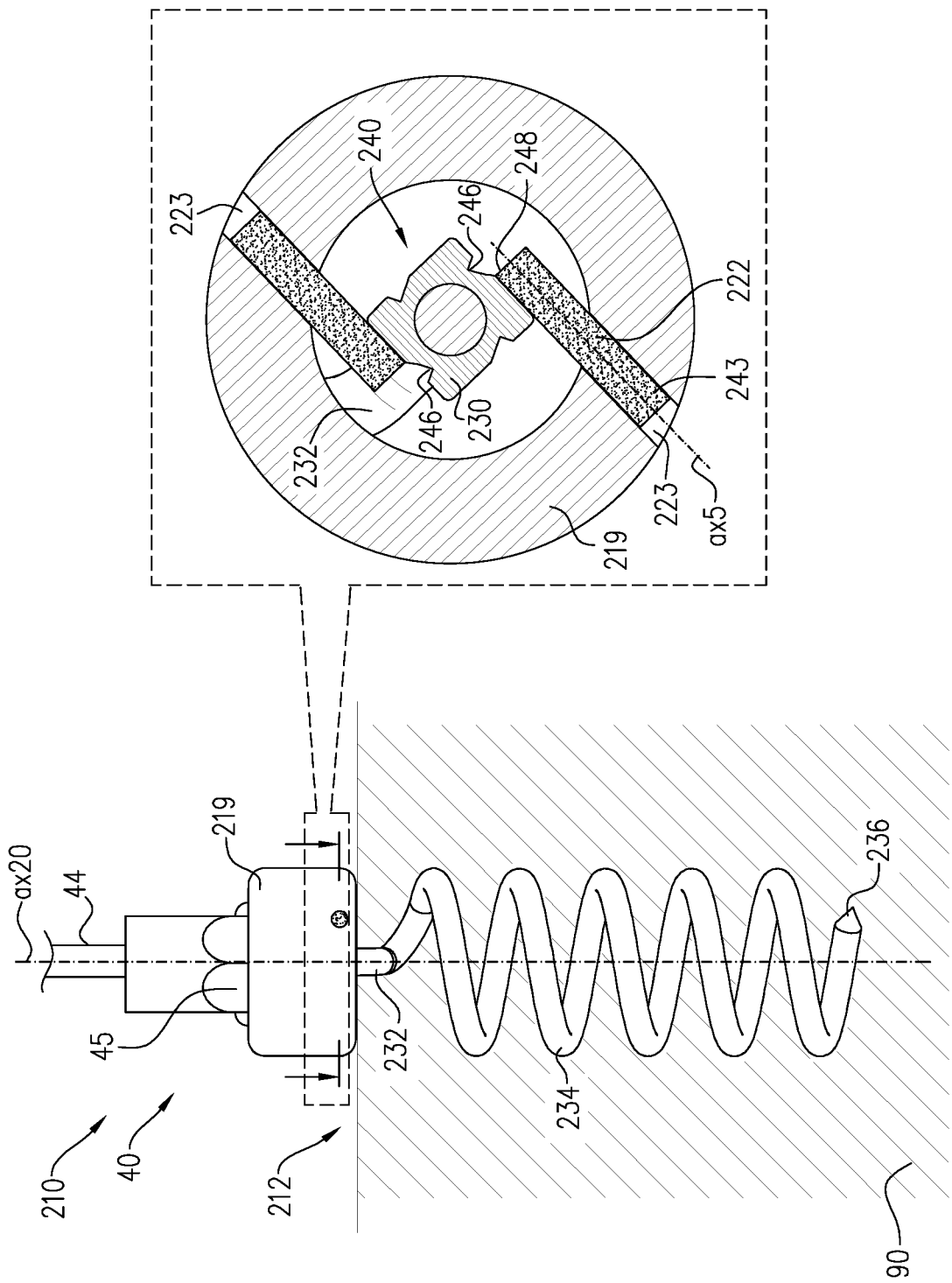
Figure 9B:
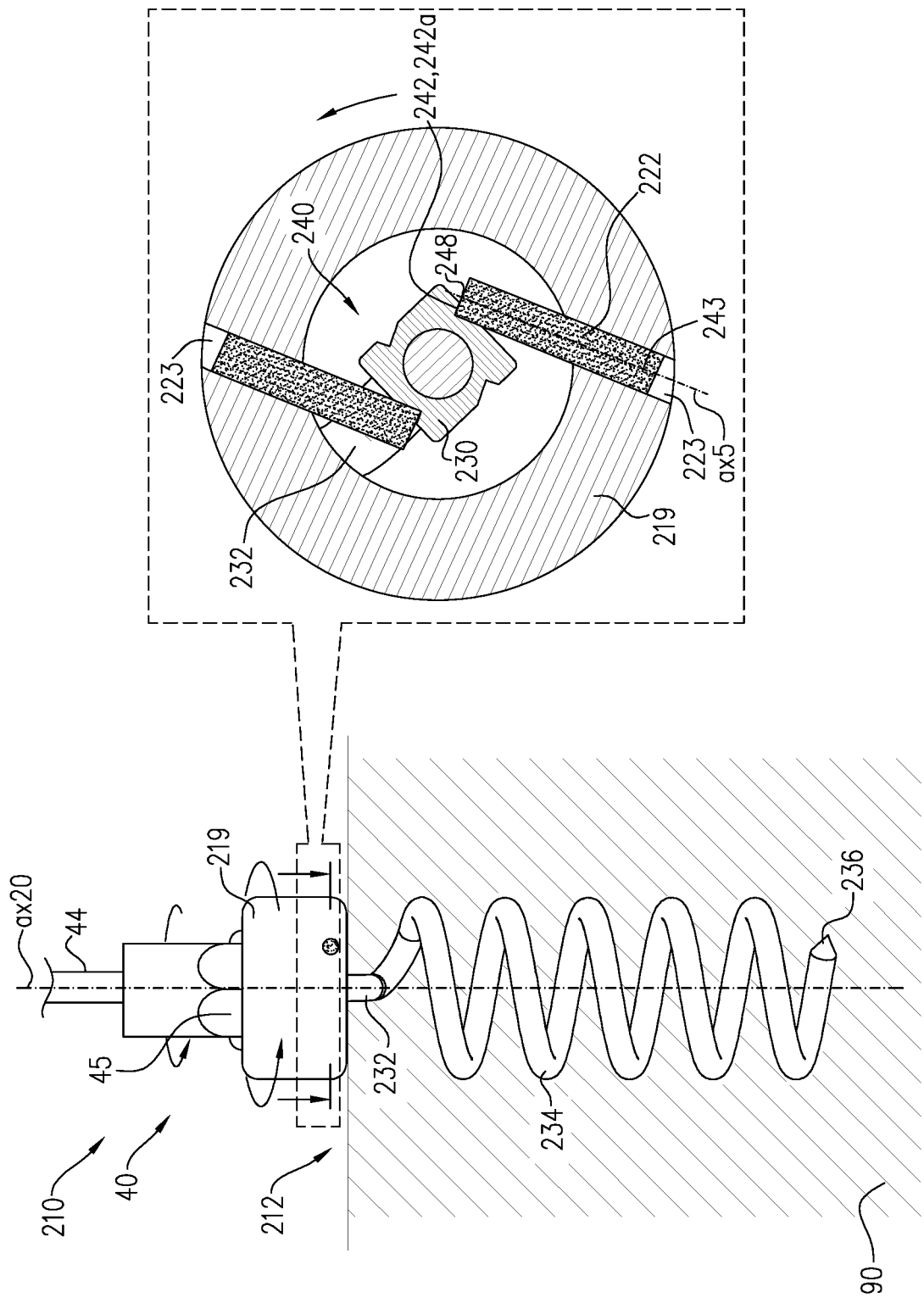

As shown in FIGS. 9A-B, removal of anchor 212 from tissue 90 is accomplished by applying reverse torque to interface 241, such that pins 222 revolve about longitudinal axis ax20 in the second rotational direction, while the pins contact gear 230.

However, the manner in which pins 222 of anchor 212 contact gear 230 while revolving about longitudinal axis ax20 in the second rotational direction is different from the manner in which the pins contact the gear while revolving in the first direction. As shown in FIG. 9B, reverse rotation of driver interface 241 can cause some reverse rotation of pins 222 in relation to gear 230 (e.g., "backlash"). As shown, a degree of backlash permitted by reverse rotation of pins 222 is typically limited to less than a quarter turn.

FIG. 9B shows pins 222 having rotated in the second direction until the pins engage gear 230 (e.g., until end-portions 248 are latched into notches 246). In some applications, once end-portions 248 fit into notches 246, backlash is stopped, and pins (e.g., torque-applying portions 242b) transfer torque from interface 241 to gear 230, this time in the second direction.

Figure 9C:
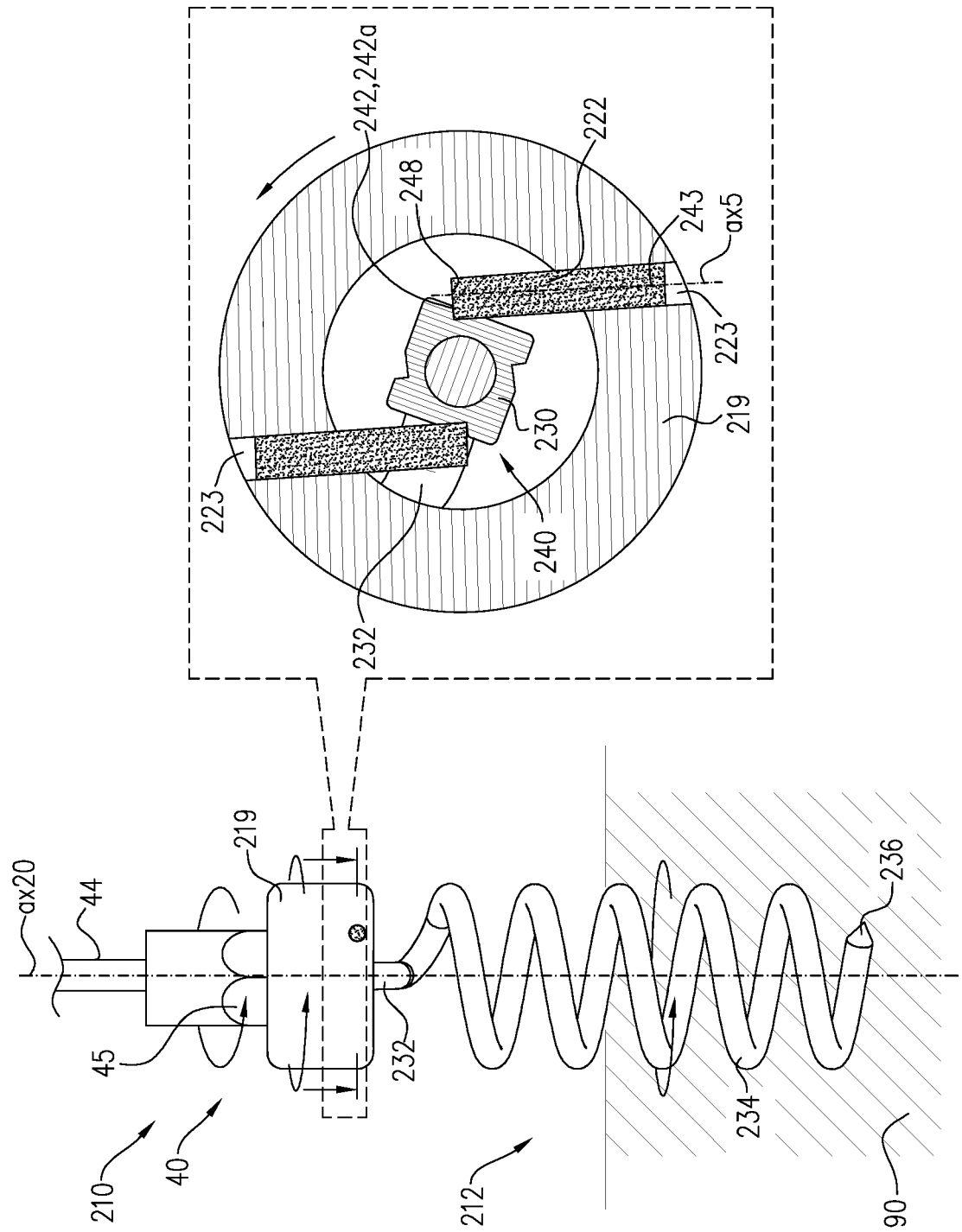

Thereby, slip clutch 240 may allow reverse torque that exceeds the torque threshold to be transferred from driver interface 241 to gear 230. As shown in FIGS. 9B-C, latching of end-portions 248 of pins 222 into notches 246 facilitates unscrewing anchor 212 from tissue 90, by gear 230 and anchoring portion 234 rotating with driver interface 241, in response to pin 222 revolving about longitudinal axis ax20 in the second direction.

Referring again to FIGS. 1A-9C, the tissue anchors described herein can be used to fasten one tissue to another, and/or to secure another element (e.g., an implant) to tissue. For example, a system for treating a patient can include an implant that is secured to the tissue with any of the tissue anchors described herein.

The tissue anchors described herein can be used for anchoring to cardiac tissue, such as to an atrial wall, a ventricular wall, or a valve annulus of a heart. For some applications, one or more of the tissue anchors described herein can be used to secure, to cardiac tissue, an implant. For some applications, one or more of the tissue anchors described herein can be used to secure, to cardiac tissue, a tether or contraction member (e.g., contraction wire, contraction ribbon, contraction suture, etc.) that is to be tensioned in order to change a shape and/or function of the heart. For example, one or more of the tissue anchors described herein can be used to secure, to ventricular tissue, a tether or contraction member that is also secured to a valve leaflet. For some applications, a plurality of tissue anchors described herein can be used to secure, to a valve annulus, an annuloplasty structure, e.g., with the anchors serving, mutatis mutandis, in place of the anchors described in one or more of the embodiments disclosed in U.S. Pat. No. 9,949,828 to Sheps et al., US Patent Application Publication 2020/0015971 to Brauon et al., PCT Application PCT/IB2020/060044 to Kasher et al. (which published as WO 2021/084407), and/or U.S. Provisional Patent Application 63/147,699 to Shafigh et al., each of which is incorporated herein by reference. Furthermore, one or more features of the tissue anchors described in these incorporated references cab be provided on any of the tissue anchors described hereinabove. For example, the scope of the present disclosure includes modifying any of the anchors described hereinabove to include (e.g., on the crown of the tissue anchor) an eyelet or rotating eyelet, such as described in one of these incorporated references, e.g., in order to slidably couple the anchor to a tether or contraction member that is to be anchored around an annulus of a heart valve and subsequently tensioned in order to perform transluminal annuloplasty. For some applications, an implant comprises a tether/contraction member and one or more of the anchors described herein.

The present invention is not limited to what has been particularly shown and described herein. Rather, the scope of the invention includes both combinations and subcombinations of the various features described herein, as well as variations and modifications thereof that are not in the prior art, which would occur to persons skilled in the art upon reading the foregoing description. The treatment techniques, methods, operations, steps, etc. described or suggested herein can be performed on a living animal or on a non-living simulation, such as on a cadaver, cadaver heart, simulator (e.g., with the body parts, tissue, etc. being simulated), etc.

The invention claimed is:

1. A system for use with tissue of a subject, the system comprising:
   a driver; and
   a tissue anchor, the tissue anchor comprising:
      an anchoring portion configured to be screwed distally into the tissue by being rotated about a longitudinal axis of the anchor; and
      a crown, coupled to a proximal portion of the anchoring portion, defining a tissue-facing surface, and comprising:
         an anchor head fixedly coupled to the anchoring portion, such that screwing the anchoring portion into the tissue moves the anchor head distally along the longitudinal axis toward the tissue,
         a driver interface, configured to be engaged by the driver, and
         a socket, fixedly coupled to the driver interface, and shaped to receive the anchor head within the socket, the tissue-facing surface facing distally away from the socket,
      wherein the tissue anchor has:
         a first state in which the anchor head is seated snugly within the socket, such that torque applied by the driver to the driver interface rotates the socket, the anchor head, and the anchoring portion, thereby facilitating screwing of the anchoring portion into the tissue, and
         a second state in which the anchor head is disposed distally from the socket, such that torque applied by the driver to the driver interface rotates the socket relative to the anchor head and the anchoring portion, and
      wherein the tissue anchor is configured to transition from the first state to the second state, responsively to the anchoring portion having been screwed into the tissue sufficiently deep such that the tissue resists further distal movement of the tissue-facing surface while the screwing of the anchoring portion into the tissue pulls the anchor head distally out of the socket.

2. The system according to claim 1, wherein the driver interface defines a floor that separates the driver from the anchor head while the driver interface is engaged by the driver.

3. The system according to claim 1, wherein the anchor head is shaped such that a transverse cross-section of the anchor head defines a non-circular profile.

4. The system according to claim 3, wherein the anchor head is shaped such that the transverse cross-section of the anchor head defines a plurality of lateral surfaces.

5. The system according to claim 3, wherein the anchor head is shaped such that the transverse cross-section of the anchor head defines at least one of a polygon, a square, and a hexagon.

6. The system according to claim 1, wherein the tissue is tissue of a heart of the subject, and wherein the tissue anchor is transluminally advanceable to the heart.

7. The system according to claim 6, wherein the driver comprises a flexible shaft and a driver head at a distal end of the shaft, such that the anchor driver is transluminally advanceable to the heart.

8. The system according to claim 1, wherein the crown comprises a casing, the casing dimensioned to define:
   the driver interface,
   the socket,
   the tissue-facing surface, and
   a free zone disposed between the socket and the tissue-facing surface,
wherein, while the anchor is in the second state, the anchor head is disposed within the free zone.

9. The system according to claim 8, wherein the anchor head is rotatable with respect to the socket while the anchor head is disposed in the free zone.

10. The system according to claim 8, wherein the driver comprises a driver head, the driver head shaped to define a shoulder, the shoulder:
- positioned on a side of the driver head, and
- dimensioned such that, while the driver interface is engaged by the driver head, the shoulder contacts a proximal surface of the casing.

11. The system according to claim 8, further comprising a spring disposed within the casing, between the anchor head and the tissue-facing surface, wherein the anchor is configured such that while the anchor transitions from the first state to the second state:
- screwing the anchoring portion into the tissue pulls the anchor head distally out of the socket, compressing the spring.

12. The system according to claim 11, wherein the anchor is configured such that while the anchor transitions from the first state to the second state, screwing the anchoring portion into the tissue pulls the anchor head distally out of the socket, compressing the spring and pressing the tissue-facing surface against the tissue.

13. The system according to claim 11, wherein the anchor is configured such that while the anchor transitions from the first state to the second state, screwing the anchoring portion into the tissue pulls the anchor head distally out of the socket, compressing the spring while the anchor head is:
- partially disposed within the socket, and
- partially disposed within the free zone.

14. The system according to claim 1, further comprising an implant, wherein the tissue anchor is configured to secure the implant to the tissue.

15. The system according to claim 14, wherein the implant comprises a tether or contraction member, wherein the tissue anchor is configured to secure the tether or contraction member to the tissue such that applying tension to the tether or contraction member changes a shape and/or size of the tissue.

* * * * *